(12) United States Patent
Lupo et al.

(10) Patent No.: US 11,313,741 B2
(45) Date of Patent: Apr. 26, 2022

(54) PACKAGING TECHNOLOGIES FOR TEMPERATURE SENSING IN HEALTH CARE PRODUCTS

(71) Applicant: Apple Inc., Cupertino, CA (US)

(72) Inventors: Pierpaolo Lupo, Singapore (SG); Bilal Mohamed Ibrahim Kani, Singapore (SG); Kishore N. Renjan, Singapore (SG); Kyusang Kim, Singapore (SG); Manoj Vadeentavida, Singapore (SG)

(73) Assignee: Apple Inc., Cupertino, CA (US)

(*) Notice: Subject to any disclaimer, the term of this patent is extended or adjusted under 35 U.S.C. 154(b) by 224 days.

(21) Appl. No.: 16/711,247

(22) Filed: Dec. 11, 2019

(65) Prior Publication Data

US 2021/0181039 A1    Jun. 17, 2021

(51) Int. Cl.

| | |
|---|---|
| H01L 23/538 | (2006.01) |
| G01K 13/20 | (2021.01) |
| G01K 1/08 | (2021.01) |
| G01K 7/02 | (2021.01) |
| G01K 7/16 | (2006.01) |
| H01L 23/00 | (2006.01) |
| H01L 23/28 | (2006.01) |
| H01L 23/498 | (2006.01) |

(52) U.S. Cl.
CPC ............. *G01K 13/20* (2021.01); *G01K 1/08* (2013.01); *G01K 7/02* (2013.01); *G01K 7/16* (2013.01); *H01L 23/00* (2013.01); *H01L 23/28* (2013.01); *H01L 23/4985* (2013.01); *H01L 23/538* (2013.01)

(58) Field of Classification Search
CPC ..... H01L 23/498–49894; H01L 23/538–5389; H01L 23/12–15; H01L 2924/151–15798
See application file for complete search history.

(56) References Cited

U.S. PATENT DOCUMENTS

| | | | |
|---|---|---|---|
| 6,180,867 B1 * | 1/2001 | Hedengren | ............. G01K 3/14 136/201 |
| 8,905,635 B2 | 12/2014 | Clark et al. | |
| 9,778,688 B2 | 10/2017 | Tang et al. | |
| 10,260,961 B2 | 4/2019 | Ferguson et al. | |

(Continued)

FOREIGN PATENT DOCUMENTS

| | | |
|---|---|---|
| CN | 206364003 U | 7/2017 |
| EP | 2312288 B1 | 9/2009 |

(Continued)

OTHER PUBLICATIONS

PCT/US2020/061987, "PCT International Search Report and the Written Opinion of the International Searching Authority", dated Jun. 8, 2021, 19 pages.

*Primary Examiner* — Tucker J Wright
(74) *Attorney, Agent, or Firm* — Aikin & Gallant, LLP

(57) ABSTRACT

Temperature sensor packages and methods of fabrication are described. The temperature sensor packages in accordance with embodiments may be rigid or flexible. In some embodiments the temperature sensor packages are configured for touch sensing, and include an electrically conductive sensor pattern such as a thermocouple or resistance temperature detector (RTD) pattern. In some embodiments, the temperature sensor packages are configured for non-contact sensing an include an embedded transducer.

21 Claims, 28 Drawing Sheets

(56) References Cited

U.S. PATENT DOCUMENTS

| | | |
|---|---|---|
| 10,411,329 B2 | 9/2019 | Cardinal et al. |
| 2017/0191879 A1 | 7/2017 | Martin |
| 2017/0207524 A1* | 7/2017 | Cardinali ................ H01Q 9/42 |
| 2018/0003569 A1* | 1/2018 | Eid ....................... H01L 41/047 |
| 2018/0028072 A1 | 2/2018 | Shi |
| 2018/0084667 A1 | 3/2018 | Saeidi et al. |
| 2019/0082968 A1 | 3/2019 | Karnik et al. |
| 2021/0265317 A1* | 8/2021 | Leirer ................ H01L 25/0753 |

FOREIGN PATENT DOCUMENTS

| | | |
|---|---|---|
| TW | 200534182 A | 10/2005 |
| TW | M454627 U | 6/2013 |
| TW | 201626514 A | 7/2016 |
| WO | 2010100870 A1 | 9/2010 |

\* cited by examiner

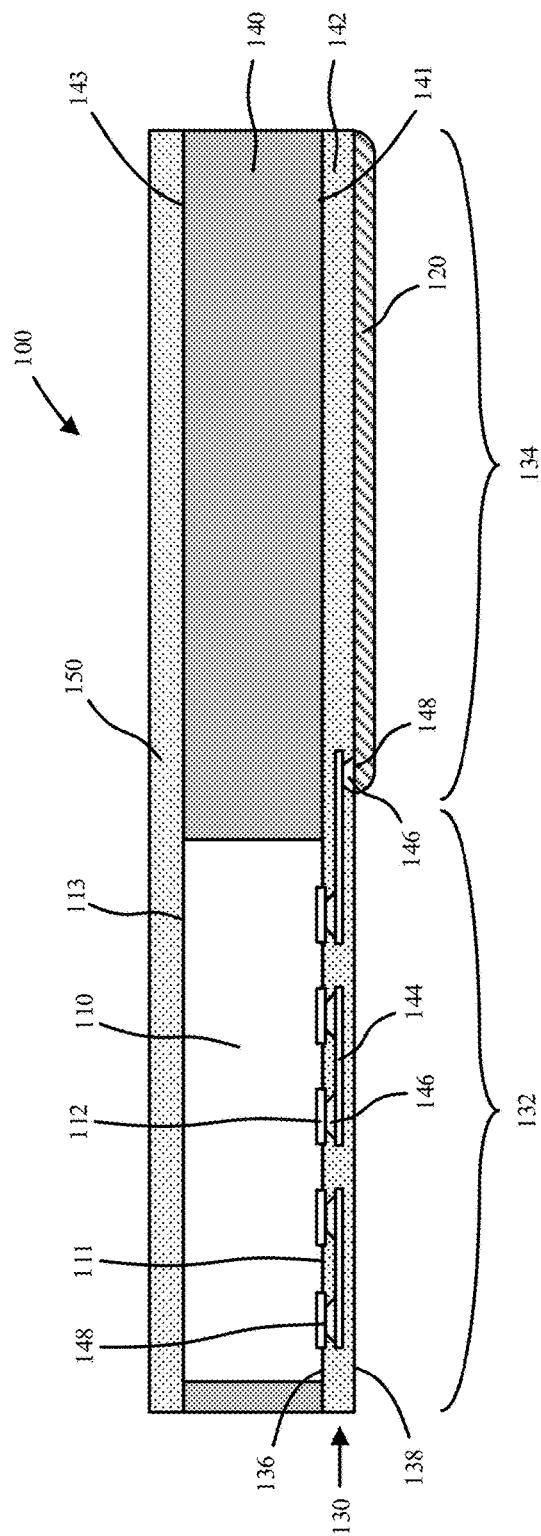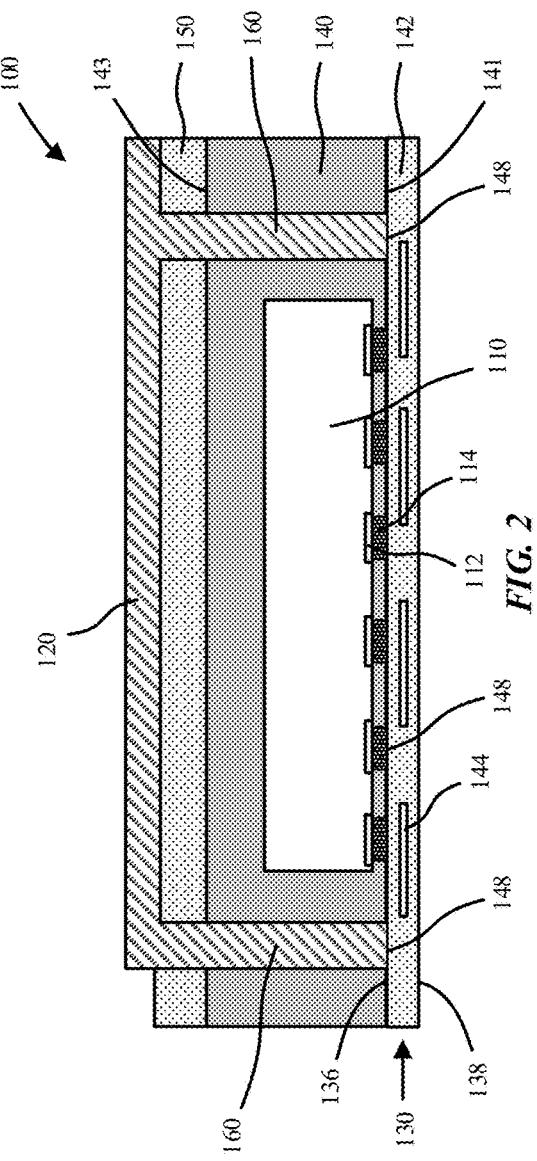

PACKAGING TECHNOLOGIES FOR TEMPERATURE SENSING IN HEALTH CARE PRODUCTS

BACKGROUND

Field

Embodiments described herein relate to microelectronic packaging, and more particular to temperature sensor packaging technologies.

Background Information

Wearable health devices are increasingly integrating a broad variety of sensors to better monitor heath status of users. With the development of packaging technologies such as system in package, embedded die, semiconductor very-large-scale integration (VLSI) technologies and so on it has become possible to develop miniaturized systems and devices. Skin temperature is one of the vital signs for patient's health.

SUMMARY

Temperature sensor packages, methods of fabrication, and products incorporating such packages are described. For example, the temperature sensor packages may be secured within (e.g. within a housing) of a portable electronic device, or secured to a fabric of a wearable device. The temperature sensor packages may be characterized as suitable for touch or non-contact temperature sensing. In some embodiments, touch sensing configurations may be characterized as having a back side electrically conductive sensor pattern, where the electrically conductive sensor pattern is over a back side of a chip (e.g. controller chip for the package). In some embodiments, the touch sensing configurations may be characterized as having a front side electrically conductive sensor pattern, where the electrically conductive sensor pattern on a front side of the chip. In some embodiments, a non-contact temperature sensor package may include an embedded transducer.

In an embodiment, a temperature sensor package includes a routing layer, a chip mounted face down on the routing layer, an insulating layer encapsulating the chip on the routing layer, a plurality of through vias through the insulating layer, and an electrically conductive sensor pattern over the insulating layer and coupled to the plurality of through vias. The electrically conductive sensor pattern may be directly over a back side of the chip. In an embodiment, the chip is solder bonded to the routing layer.

Various techniques may be used for the formation of the electrically conductive sensor pattern and through vias. In some embodiments screen printing or similar dispensing techniques are used. In an embodiment, at least a portion of the electrically conductive temperature sensor pattern and at least one of the plurality of through vias is formed of a same material. In one implementation the same material includes coalesced metallic particles forming the portion of the electrically conductive temperature sensor pattern and the one of the plurality of through vias. In some embodiments laser direct structuring (LDS) is utilized. In one implementation the insulating layer is an LDS compatible material including a dispersed non-conductive metal organic compound, and the plurality of vias include a nucleation layer of metal particles of the metal in the dispersed non-conductive metal organic compound. Similarly, the electrically conductive sensor pattern can optionally include a nucleation layer pattern of metal particles of the metal in the dispersed non-conductive metal organic compound.

The electrically conductive sensor patterns have different modes of operation, such as thermocouple or resistance temperature detector (RTD) pattern. In an embodiment, the electrically conductive sensor pattern is a thermocouple pattern with a first pattern of a first conductive material and a second pattern of a second conductive material different from the first conductive material. In an embodiment, the plurality of through vias includes a first via connected to the first pattern, and a second via connected to the second pattern. In a specific implementation, the first via includes the first conductive material, and the second via includes the second conductive material, though this is not required. In an embodiment, the electrically conductive sensor pattern is an RTD pattern, which may be formed of the same or different material than the plurality of through vias.

In an embodiment, a temperature sensor package includes a routing layer with a chip contact area, and a touch area adjacent the chip contact area. The touch area may include an electrically conductive sensor pattern electrically connected to the chip contact area, while a chip is bonded to the routing layer in the chip contact area. Such a configuration may be characterized as a front side electrically conductive sensor pattern. In an embodiment, the chip is encapsulated in an insulating layer laterally surrounding the chip on a top side of the routing layer, and the insulating layer spans the touch area. In an embodiment, the chip is mounted on a first side of the routing layer, and a second side of the routing layer opposite the first side includes the electrically conductive sensor pattern. In an embodiment, the routing layer includes a rigid-flex connection, the chip is mounted on a rigid portion of the rigid-flex connection and the electrically conductive sensor pattern is part of a flexible portion of the rigid-flex connection.

In an embodiment, a temperature sensor package includes a routing layer including a top side and a bottom side, a cavity formed in the bottom side of the routing layer, a transducer mounted within the cavity, and a chip mounted on the top side of the routing layer and in electrical connection with the transducer. An optical window may be formed over a surface of the transducer. An insulating layer such as a molding compound may optionally encapsulate the routing layer and the chip.

BRIEF DESCRIPTION OF THE DRAWINGS

FIG. 1 a cross-sectional side view illustration of a temperature sensor package with embedded chip and front side electrically conductive sensor pattern in accordance with an embodiment.

FIG. 2 is a cross-sectional side view illustration of a temperature sensor package with embedded chip and back side electrically conductive sensor pattern in accordance with an embodiment.

DETAILED DESCRIPTION

Figure 3A:
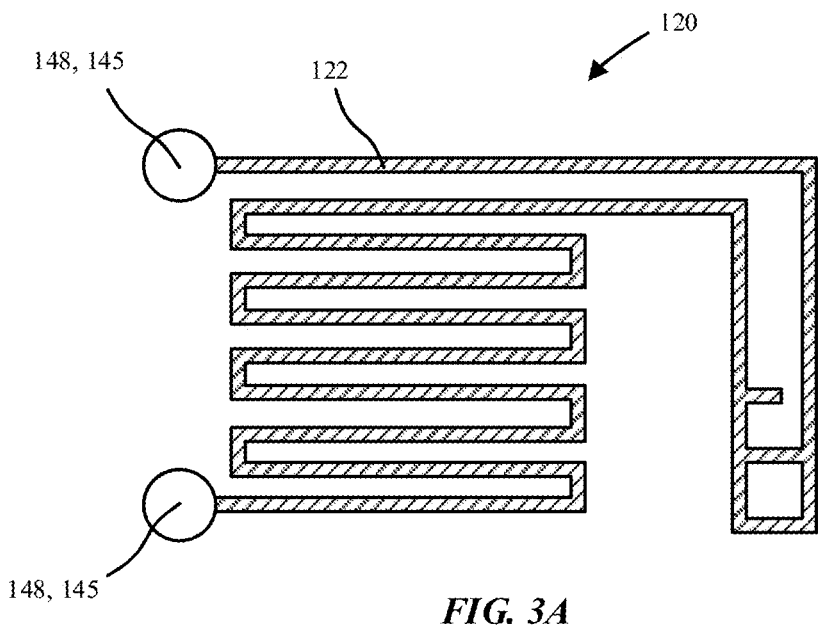
FIG. 3A is a schematic top view illustration of a resistance temperature detector (RTD) pattern in accordance with an embodiment.

Embodiments describe temperature sensor packages, methods of fabrication, and products incorporating such packages. In particular, embodiments describe temperature sensor packaging solutions that can be embedded into wearable heath devices for sensing temperature, such as skin temperature.

In one aspect, various touch sensitive temperature sensor packages are described. Such packaging solutions may allow for integration into flexible structures and do not require an optical window or transducer for operation.

In an embodiment, a temperature sensor package includes a routing layer, a chip (such as a digital controller) mounted face down on the routing layer, an insulating layer that encapsulates the chip on the routing layer, and a plurality of through vias through the insulating layer. An electrically conductive sensor pattern such as a resistance temperature detector (RTD) pattern or thermocouple is located over the insulating layer and is coupled to the plurality of through vias.

In an embodiment, a temperature sensor package includes a routing layer that includes a chip contact area and a touch area adjacent the chip contact area. The touch area may include an electrically conductive sensor pattern electrically connected to the chip contact area, while a chip is bonded to the routing layer in the chip contact area.

In another aspect, an infrared (IR) temperature sensor package is described. Such a packaging solution may allow for space savings due to an embedded thermal sensor (e.g. transducer) and provide short and flexible routing. In an embodiment, a temperature sensor package includes a routing layer (e.g. circuit board) including a top side and a bottom side. A cavity is formed in the bottom side of the routing layer, and a transducer is mounted is within the cavity. A chip is mounted on a top side of the routing layer and in electrical connection with the transducer.

The routing layers in accordance with the various embodiments described herein may be formed using various solutions such as redistribution layers or printed circuit boards (PCBs), each including one or more wiring layers and dielectric layers. Furthermore, the routing layers may be rigid or flexible, and in an embodiment may include a rigid-flex connection.

In various embodiments, description is made with reference to figures. However, certain embodiments may be practiced without one or more of these specific details, or in combination with other known methods and configurations. In the following description, numerous specific details are set forth, such as specific configurations, dimensions and processes, etc., in order to provide a thorough understanding of the embodiments. In other instances, well-known semiconductor processes and manufacturing techniques have not been described in particular detail in order to not unnecessarily obscure the embodiments. Reference throughout this specification to "one embodiment" means that a particular feature, structure, configuration, or characteristic described in connection with the embodiment is included in at least one embodiment. Thus, the appearances of the phrase "in one embodiment" in various places throughout this specification are not necessarily referring to the same embodiment. Furthermore, the particular features, structures, configurations, or characteristics may be combined in any suitable manner in one or more embodiments.

The terms "over", "to", "between", "spanning" and "on" as used herein may refer to a relative position of one layer with respect to other layers. One layer "over", "spanning" or "on" another layer or bonded "to" or in "contact" with another layer may be directly in contact with the other layer or may have one or more intervening layers. One layer "between" layers may be directly in contact with the layers or may have one or more intervening layers.

Referring now to FIG. 1 a cross-sectional side view illustration is provided of a temperature sensor package 100 with an embedded chip 110 and front side electrically conductive sensor pattern 120 in accordance with an embodiment. As illustrated, the temperature sensor package 100 can include a routing layer 130 that includes a chip contact area 132 and a touch area 134 adjacent to the chip contact area 132. In the illustrated embodiment, the touch area 134 includes the electrically conductive sensor pattern 120 that is electrically connected to chip contact area 132 and chip 110 that is bonded to the routing layer 130 in the chip contact area 132.

The chip 110 may be any type of controller chip for operation of the temperature sensor package 100, such as a digital IC, analog IC, mixed digital and analog IC, and may include additional circuitry such as an integrated amplifier. In accordance with embodiments, the chip 110 is electrically connected with the electrically conductive sensor pattern 120.

The routing layer 130 may include one or more dielectric layers 142 and wiring layers 144, and optionally vias 146. As shown, the chip 110 can be encapsulated in an insulating layer 140 on a top side 136 of the routing layer, while the bottom side 138 of the routing layer 130 includes the electrically conductive sensor pattern 120. The insulating layer 140 may be formed of a variety of materials such as an adhesive bonding or flexible molding compound and may additionally span the touch area 134 on the top side 136 of the routing layer 130. Exemplary materials include, but are not limited to, benzocyclobutene (BCB), epoxy, silicone, epoxy-based photoresist such as SU-8, etc. A top side passivation layer 150 can be formed over the chip 110 and insulating layer 140. For example, the top side passivation layer 150 may be a flexible polymer, such as polyimide. In addition to providing passivation function, the top side passivation layer 150 can be used to tune flexibility of the temperature sensor package 100. Likewise, the one or more dielectric layers 142 may be used to tune flexibility, in addition to providing an insulating substrate for the electrically conductive sensor pattern 120. The one or more dielectric layers 142 may optionally be formed of similar materials as the top side passivation layer 150. In accordance with embodiments, insulating layer 140 may provide both sealing features, and under-filling structure for the stack-up.

A temperature sensor package 100 such as that illustrated in FIG. 1 may provide a flexible encapsulated structure, which enables embedding the chip 110 into a flexible stack without a need for optical window or transducer since the electrically conductive sensor pattern 120 can be formed as part of the bottom side of the routing layer 130.

The temperature sensor package 100 can additionally be characterized as having a front side connection in which the electrically conductive sensor pattern 120 is adjacent a front side 111 of the chip 110. Furthermore, the electrically conductive sensor pattern 120 is formed on an opposite side of the routing layer 130 than the chip 110. As shown, the chip 110 is on a first side (e.g. top side 136) of the routing layer 130, while the electrically conductive sensor pattern 120 is on, or a part of, a second side (e.g. bottom side 138) of the routing layer 130 opposite the first side 136. In an embodiment, the routing layer 130 is formed directly on the front side 111 of the chip 110. For example, wiring layers 144 or vias 146 may be formed directly on chip contact pads 112. Similarly, the electrically conductive sensor pattern 120 may be formed directly on routing contacts 148, such as with the wiring layers 144 or vias 146 on an opposite side of the routing layer 130.

FIG. 2 a cross-sectional side view illustration of a temperature sensor package 100 with embedded chip 110 and back side electrically conductive sensor pattern 120 in accordance with an embodiment. A shown, the temperature sensor package 100 can include a routing layer 130, a chip 110 mounted face down on the routing layer 130, an insulating layer 140 encapsulating the chip on the routing layer 130, and a plurality of through vias 160 through the insulating layer 140. For example, the through vias 160 may extend between a first (e.g. top) surface 143 and second (e.g. bottom) surface 141 of the insulating layer 140 to make contact with the routing contacts 148 of the routing layer 130. In the illustrated embodiment, an electrically conductive sensor pattern 120 is formed over the insulating layer (e.g. over the top surface 143) and is coupled to the plurality of through vias 160. Furthermore, the electrically conductive sensor pattern 120 may be directly over a back side 113 of the chip 110.

The electrically conductive sensor pattern 120 may be formed of one or more materials and may be formed of the same or different materials than the plurality of through vias 160. In an embodiment, at least a portion of the electrically conductive temperature sensor pattern 120 and at least one of the plurality of through vias 160 is formed of a same material. The particular material may be dependent upon method of manufacture, such as plating (electroplating, electroless plating), printing, dispensing, etc. For example, plating techniques may include seed and bulk layers, while printing or dispensing techniques may include a matrix of coalesced metallic particles (which may be mixed with an adhesive such as polymer or glass).

Figure 3B:
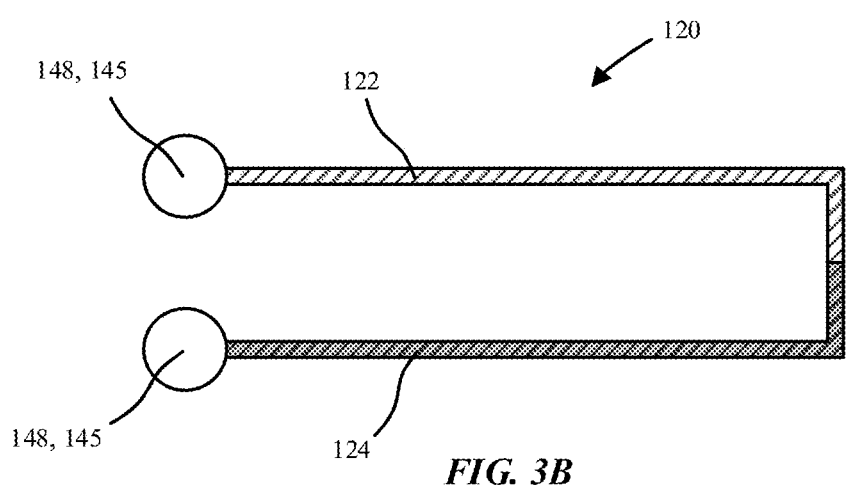
FIG. 3B is a schematic top view illustration of a thermocouple pattern in accordance with an embodiment.

Referring now to FIGS. 3A-3B the electrically conductive sensor pattern 120 may have a variety of different shapes depending upon function. For example, FIG. 3A is a schematic top view illustration of an exemplary resistance temperature detector (RTD) pattern, while FIG. 3B is a schematic top view illustration of an exemplary thermocouple pattern in accordance with embodiments. Referring now to FIG. 3A, an electrically conductive sensor pattern 120 in the form of an RTD pattern may include a single conductive layer 122 (or layer stack). For example, this may be a metal layer, or metal stack, or layer of coalesced metal particles for example. The conductive layer 122 may be formed of the same material or a different material than the through vias 160 of FIG. 2, for example. Referring to FIG. 3B, the electrically conductive sensor pattern 120 in the form of a thermocouple pattern may include a first layer 122 pattern of a first conductive material and a second layer 124 pattern of a second conductive material different from the first conductive material. For example, these can be different metal layers with different resistances. The first and second layers 122, 124 may be formed separately from, or with the corresponding through vias 160. In an embodiment, a first through via 160 includes a first conductive material of the corresponding first layer 122, and the second through via 160 includes a second conductive material of the corresponding second layer 124. For example, a dispensing technique can be used to form the conductive layers and vias of the same material. After driving off of solvent and annealing such a dispensed pasted or solution may result in a body of coalesced metallic particles (which may be mixed with an adhesive such as polymer or glass).

The temperature sensor packages 100 of FIGS. 1-2 may share several common features, though be formed using different fabrication sequences. Each fabrication technique may include coating of an electrical grade polymer such as polyimide, and placement of active and/or passive components (including the chip 110) on the electrical grade polymer. The components can then be encapsulated using a flexible bonding material, and a second electrical grade flexible polymer can be formed on the encapsulated structure. An electrically conductive sensor pattern 120 (e.g. metallization layer) can then be formed.

Figure 4:
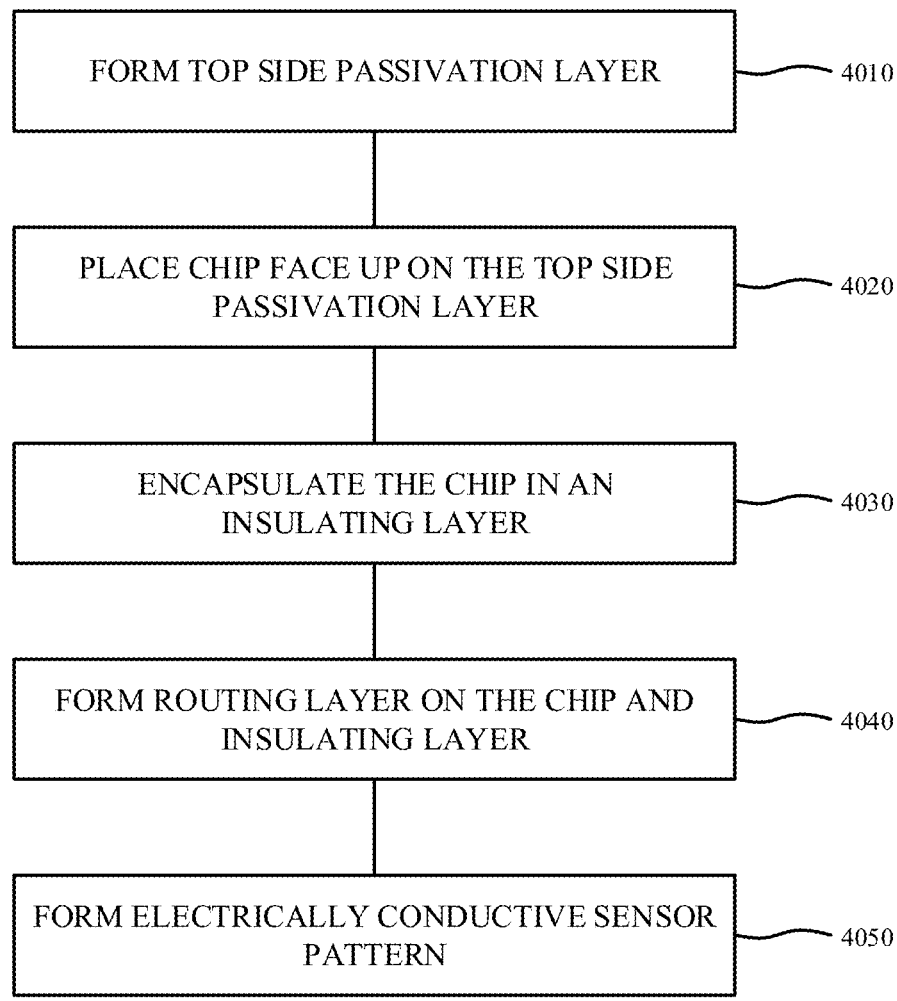
FIG. 4 is a flow diagram of a method of fabricating the temperature sensor package of FIG. 1 in accordance with an embodiment.

FIG. 4 is a flow diagram of a method of fabricating the temperature sensor package of FIG. 1 in accordance with an embodiment. FIGS. 5A-5G are schematic cross-sectional side view illustrations of a method of fabricating the temperature sensor package of FIG. 1 in accordance with an embodiment. In interest of clarity and conciseness the processing sequences of FIGS. 4 and 5A-5G are described concurrently.

Figure 5A:
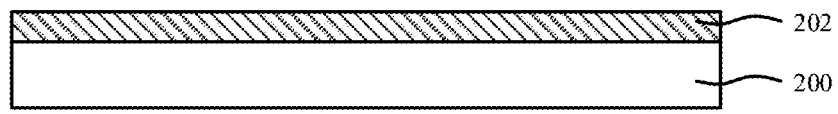
FIGS. 5A-5G are schematic cross-sectional side view illustrations of a method of fabricating the temperature sensor package of FIG. 1 in accordance with an embodiment.
Figure 5B:
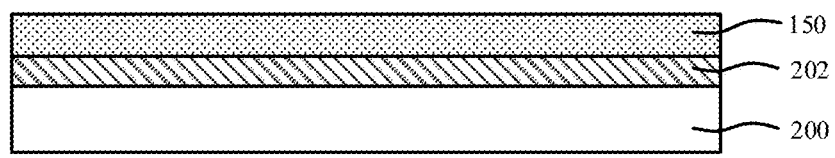
Figure 5C:
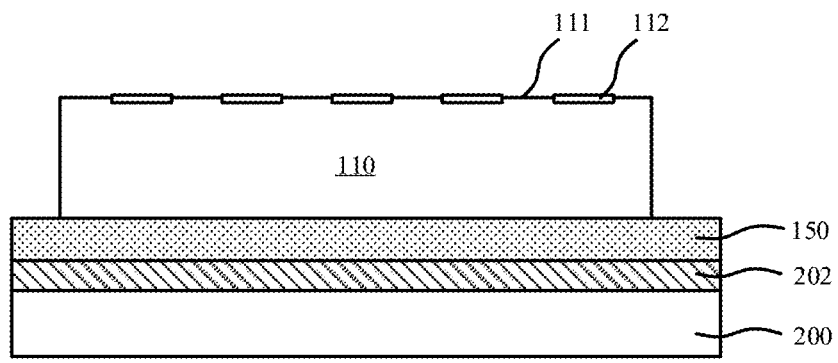
Figure 5D:
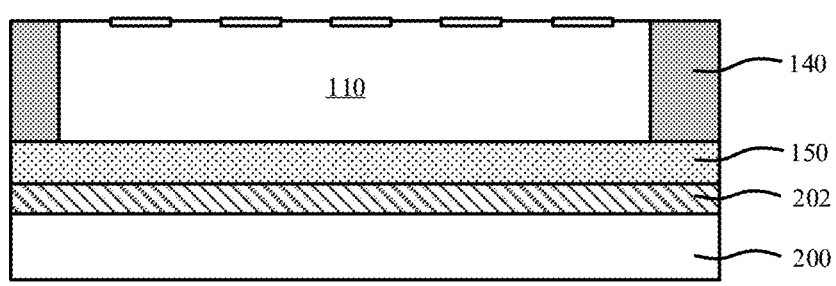
Figure 5E:
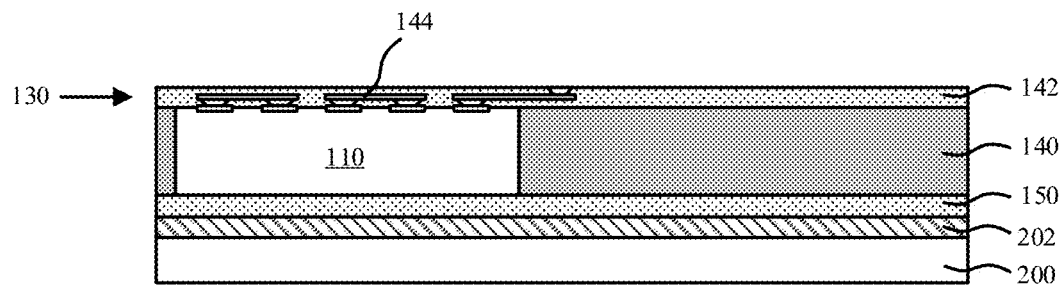
Figure 5F:
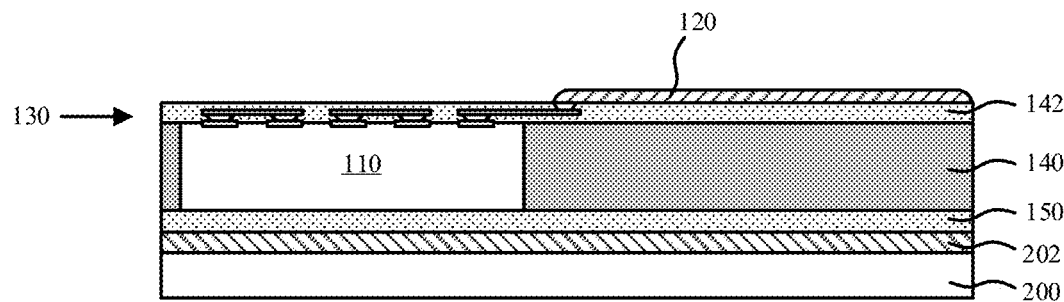
Figure 5G:
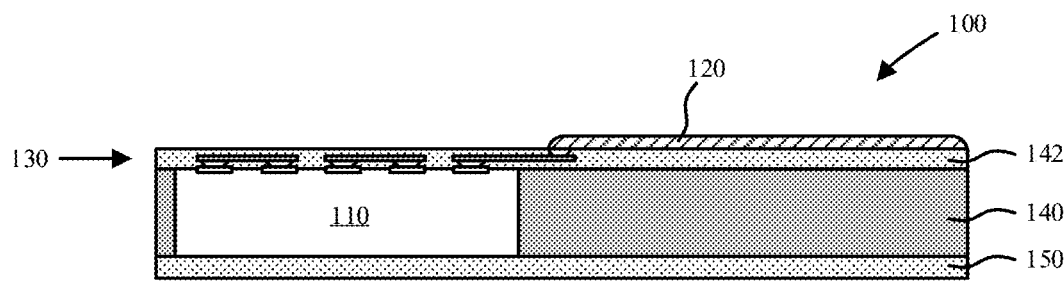

At operation 4010 a top side passivation layer 150 is formed. As shown in FIGS. 5A-5B, this sequence may include preparing a rigid carrier substrate 200 with an adhesive layer 202 such as a tape, followed by application of the top side passivation layer 150. For example, top side passivation layer 150 may be laminated, or deposited and cured. At operation 4020 the chip 110 is placed faced up on the top side passivation layer 150 as shown in FIG. 5C using a suitable technique such as a pick and place tool. Referring now to FIGS. 5D-5E, at operation 4030 the chip 110 is encapsulated in an insulating layer 140, followed by formation of routing layer 130 on the chip 110 and insulating layer 140 at operation 4040. Depending upon application, the insulating layer 140 may be a flexible material, though this is not required. Materials used for top side passivation layer 150, and dielectric layer(s) 142 of routing layer 130 may be electrical grade, and may also be flexible. The electrically conductive sensor pattern 120 may then be formed at operation 4050, followed by removal of the adhesive layer 202 and rigid carrier substrate 200 as shown in FIGS. 5F-5G. The electrically conductive sensor pattern 120 may be formed using a variety of suitable techniques such as printing or other dispensing technique, physical or chemical vapor deposition, and plating.

Figure 6:
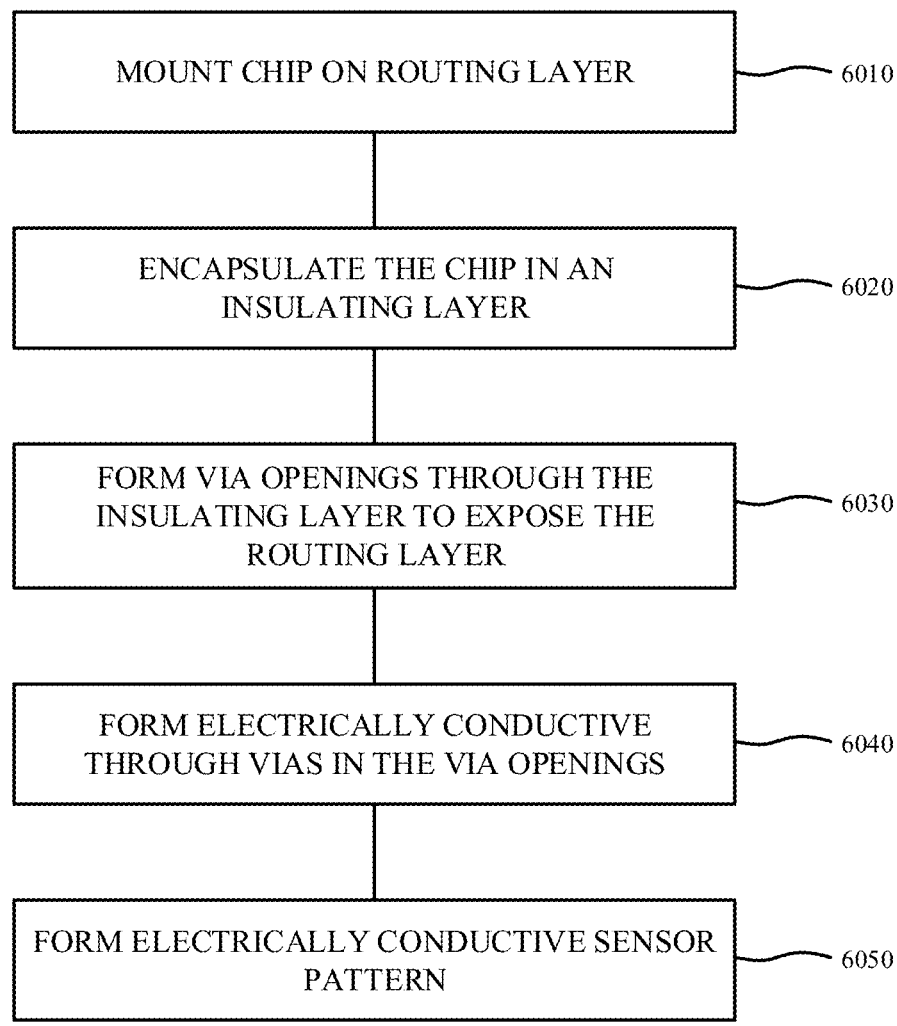
FIG. 6 is a flow diagram of a method of fabricating the temperature sensor package of FIG. 2 in accordance with an embodiment.

FIG. 6 is a flow diagram of a method of fabricating the temperature sensor package of FIG. 2 in accordance with an embodiment. FIGS. 7A-7G are schematic cross-sectional side view illustrations of a method of fabricating the temperature sensor package of FIG. 2 in accordance with an embodiment. In interest of clarity and conciseness the processing sequences of FIGS. 4 and 7A-7G are described concurrently.

At operation 6010 a chip 110 is mounted on routing layer 130. In the particular sequence illustrated in FIGS. 7A-7C, a rigid carrier substrate 200 with an adhesive layer 202 such as a tape, followed by application or formation of the routing layer 130. The routing layer 130 may be laminated, or alternatively formed using a thin film fabrication sequence of deposition and patterning dielectric layer(s) 142 and conductive (e.g. metallization) layers to form wiring layers 144, and optionally vias 146. The chip 110 can be mounted onto the routing layer 130 using a suitable technique such as pick and place with solder bumps 114, which may be bonded to routing contacts 148 for example.

Figure 7A:
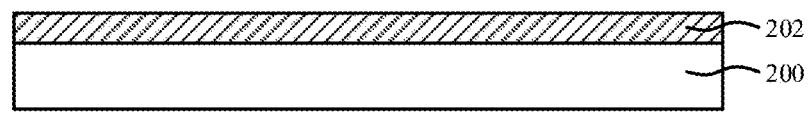
FIGS. 7A-7G are schematic cross-sectional side view illustrations of a method of fabricating the temperature sensor package of FIG. 2 in accordance with an embodiment.
Figure 7B:
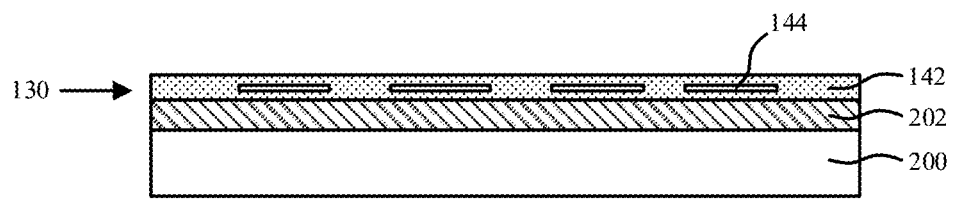
Figure 7C:
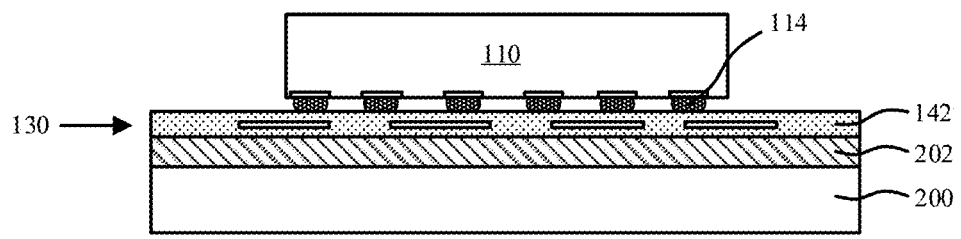
Figure 7D:
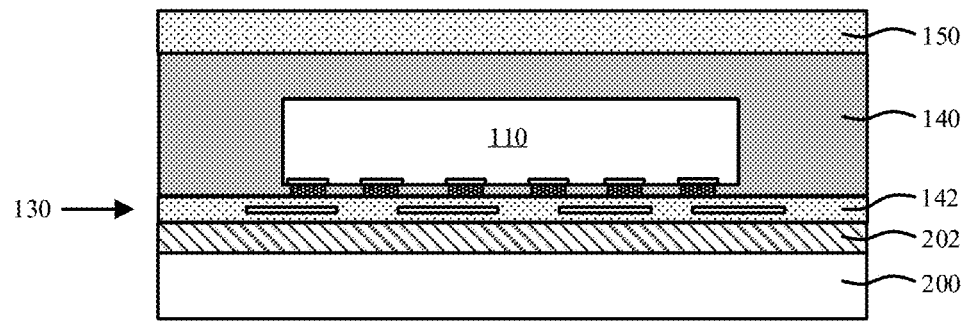
Figure 7E:
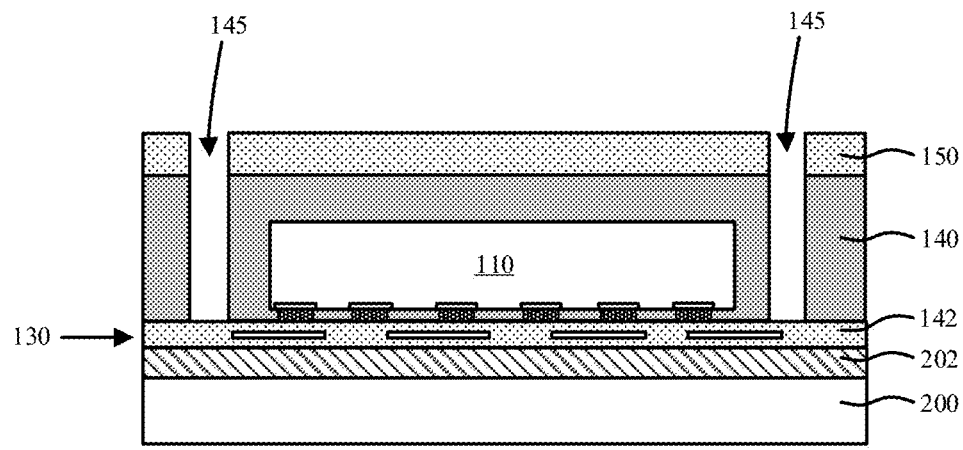

Referring now to FIG. 7D, the chip 110 may optionally be underfilled followed by encapsulation with an insulating layer 140 at operation 6020, followed by the formation of an optional top side passivation layer 150. Depending upon application, the insulating layer 140 may be a flexible material, though this is not required. Materials used for top side passivation layer 150, and dielectric layer(s) 142 of routing layer 130 may be electrical grade, and may also be flexible.

Via openings 145 are then formed through the insulating layer 140 to expose the routing layer 130 at operation 6030. Where top side passivation layer 150 is present, the via openings 145 can additionally be formed through the top side passivation layer 150. Via openings 145 may be formed using patterning techniques such as laser, drilling, or chemical etching.

Figure 7F:
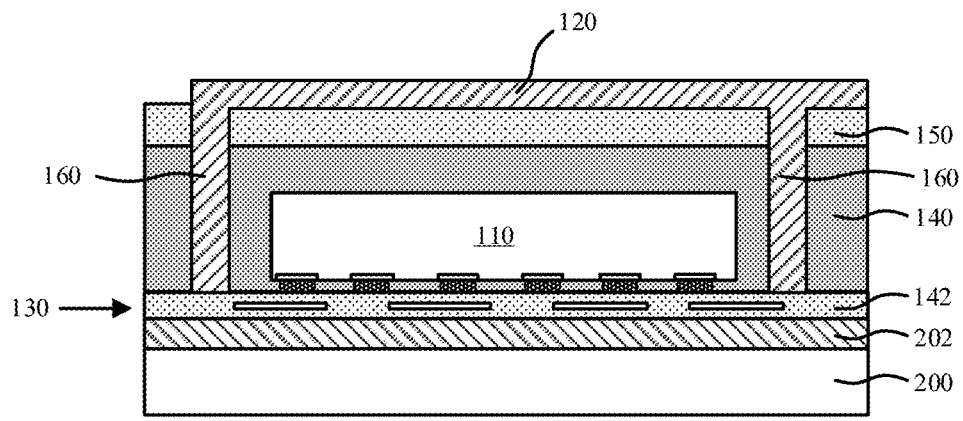
Figure 7G:
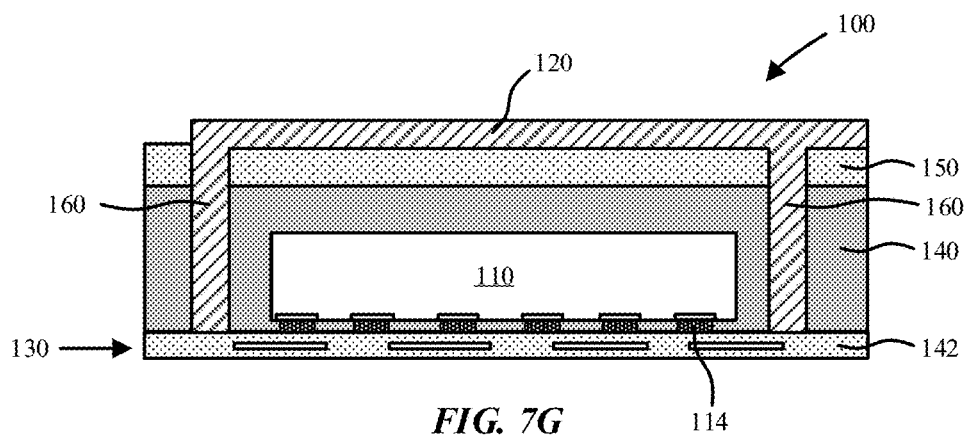

Referring now to FIG. 7F, electrically conductive through vias 160 are then formed within via openings 145 at operation 6040, and an electrically conductive sensor pattern 120 is formed at operation 6050. Operations 6040 and 6050 may be performed sequentially or simultaneously in accordance with embodiments. Furthermore, one or more same or dissimilar materials may be used to form the through vias 160 and electrically conductive sensor pattern 120. Thus, the through vias 160 and electrically conductive sensor pattern can be formed of the same materials or different materials and may be formed simultaneously (when same materials) or sequentially. Suitable materials include nickel, copper, platinum and conductive pastes that may include conductive particles that can be annealed or sintered together to form a coalesced body of particles. Exemplary deposition techniques include screen printing or other dispensing techniques, physical or chemical vapor deposition, and plating. In an embodiment, the temperature sensor package 100 includes a pair of through vias 160, each through via 160 having a different composition. For example, such as configuration may be used with a RTD pattern including layers 122, 124 formed of different materials (e.g. metals).

In the following description numerous temperature sensor packages 100 and methods of fabrication are described. In particular, the temperature sensor packages 100 may be variations of the temperature sensor packages 100 described and illustrated with regard to FIGS. 1-2. Accordingly, like features share the same reference numbers, and related descriptions may not be repeated in order to avoid unnecessarily obscuring the embodiments.

Figure 8:
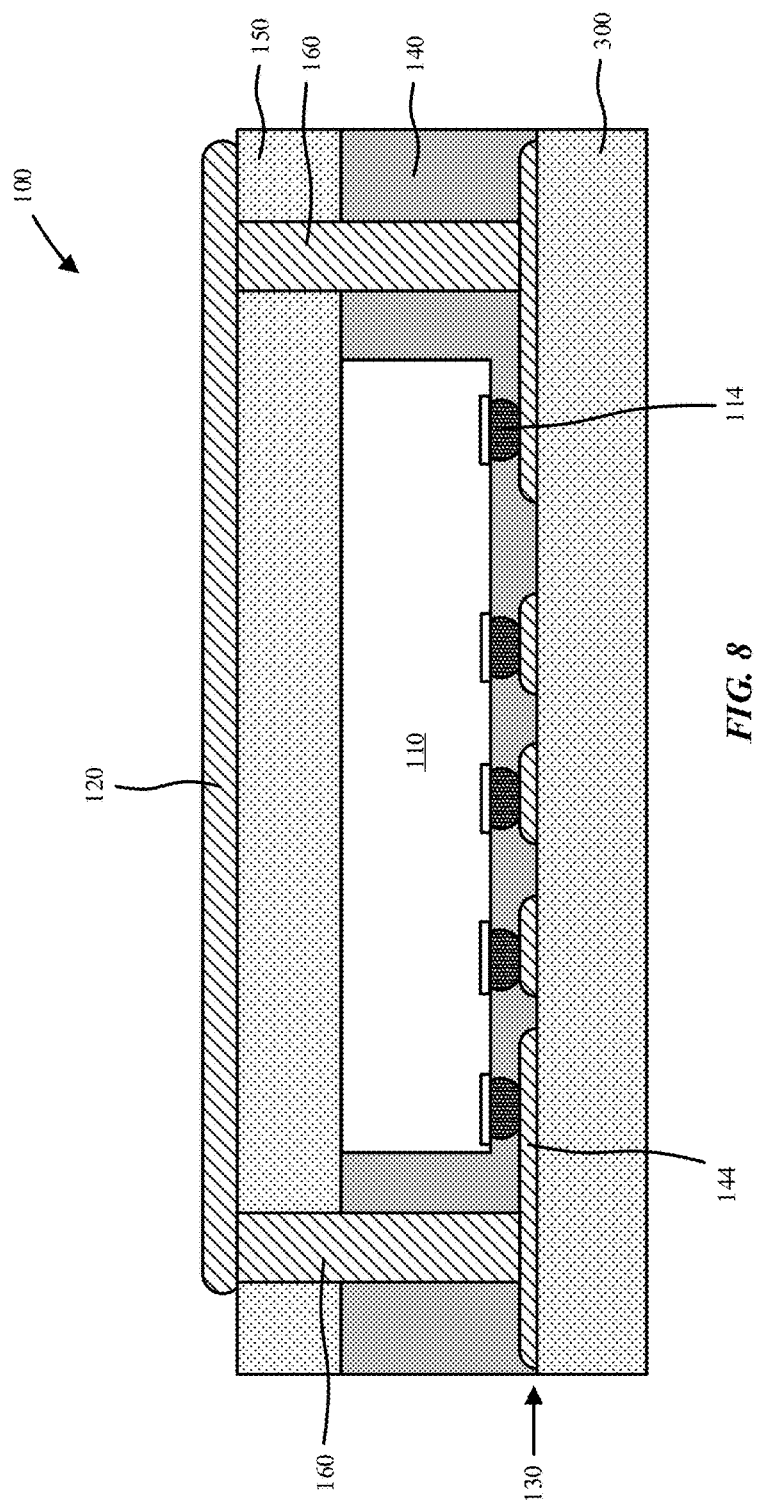
FIG. 8 is a cross-sectional side view illustration of a temperature sensor package with embedded chip and back side electrically conductive sensor pattern in accordance with an embodiment.

FIG. 8 is a cross-sectional side view illustration of a temperature sensor package 100 with embedded chip 110 and back side electrically conductive sensor pattern 120 in accordance with an embodiment. In particular, FIG. 8 shares many structural similarities to the embodiment illustrated and described with regard to FIG. 2, with one variation being that the temperature sensor package 100 of FIG. 8 can be considered a substrate-less, and in particular the routing layer 130 may be substrate-less. In an embodiment, routing layer 130 may be a single wiring layer 144, and not include additional dielectric layers. Similar to FIG. 2, the temperature sensor package 100 of FIG. 8 may optionally be a flexible stack-up.

Figure 9:
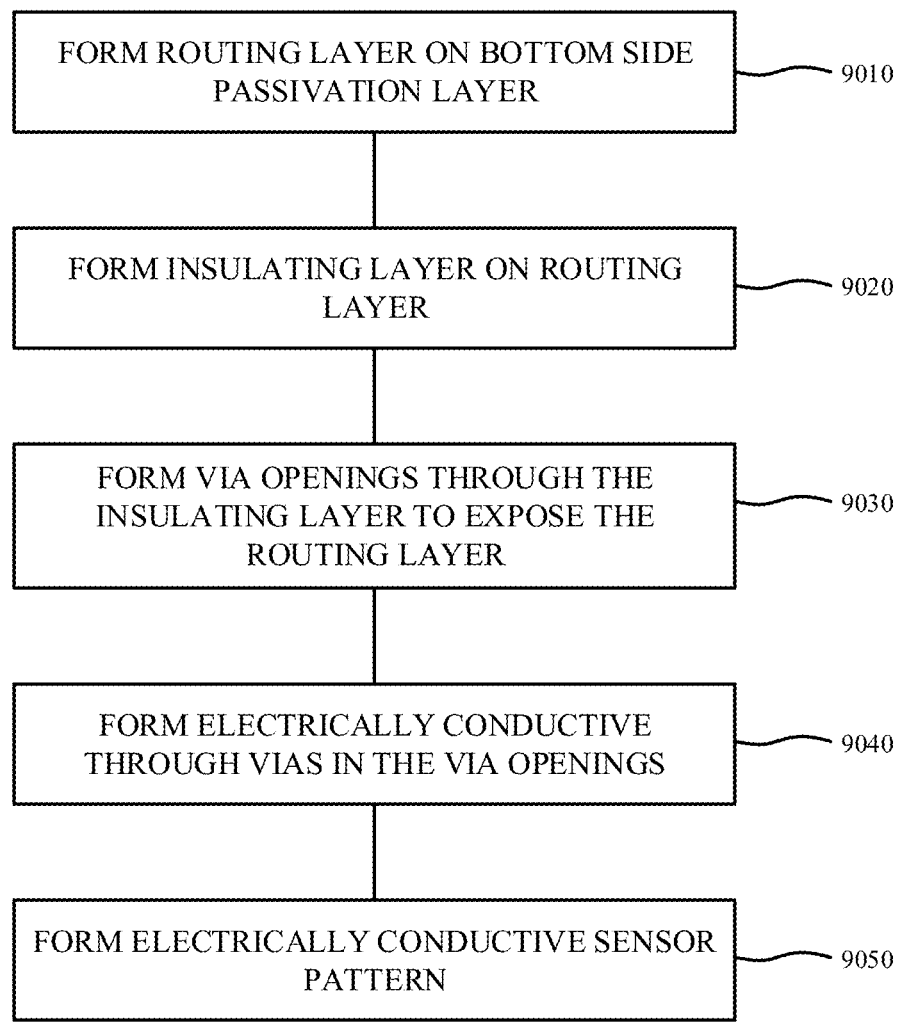
FIG. 9 is a flow diagram of a method of fabricating the temperature sensor package of FIG. 8 in accordance with an embodiment.

FIG. 9 is a flow diagram of a method of fabricating the temperature sensor package of FIG. 8 in accordance with an embodiment. FIGS. 10A-10H are schematic cross-sectional side view illustrations of a method of fabricating the temperature sensor package of FIG. 8 in accordance with an embodiment. In interest of clarity and conciseness the processing sequences of FIGS. 9 and 10A-10H are described concurrently.

Figure 10A:
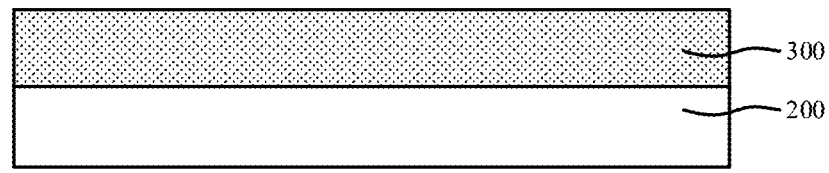
FIGS. 10A-10H are schematic cross-sectional side view illustrations of a method of fabricating the temperature sensor package of FIG. 8 in accordance with an embodiment.
Figure 10B:
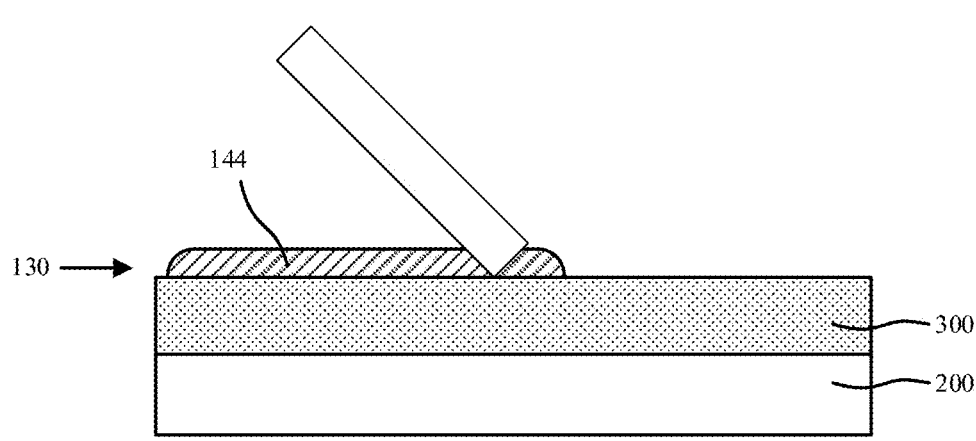

As illustrated in FIG. 10A the sequence may begin with a bottom side passivation layer 300 on a rigid carrier substrate 200. For example, the bottom side passivation layer 300 may be formed using a suitable technique such as lamination or deposition. The bottom side passivation layer 300 may be formed of similar materials as top side passivation layer 150 previously described. At operation 9010 a routing layer 130 is formed on the bottom side passivation layer 300 as shown in FIG. 10B. In an embodiment, the routing layer 130 includes a single metallization layer or wiring layer 144, which can be formed using a variety of techniques such as screen printing or other dispensing method, physical or chemical vapor deposition, and plating. Screen printing or other dispensing methods in particular may be particularly simple for manufacturing.

Figure 10C:
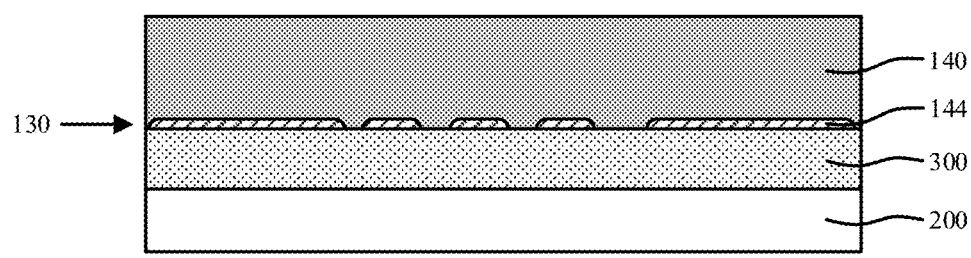
Figure 10D:
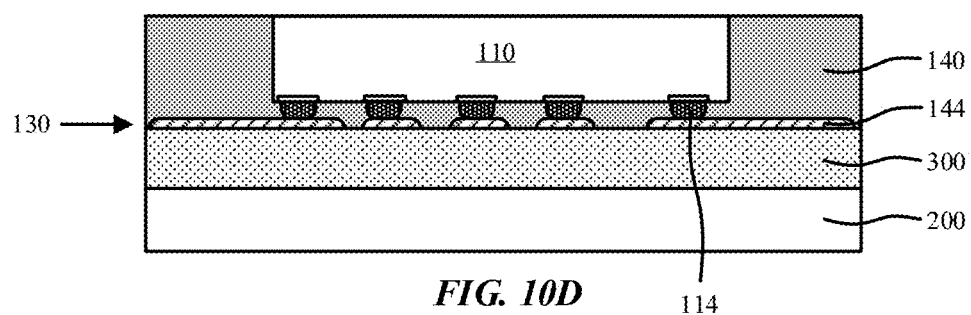
Figure 10E:
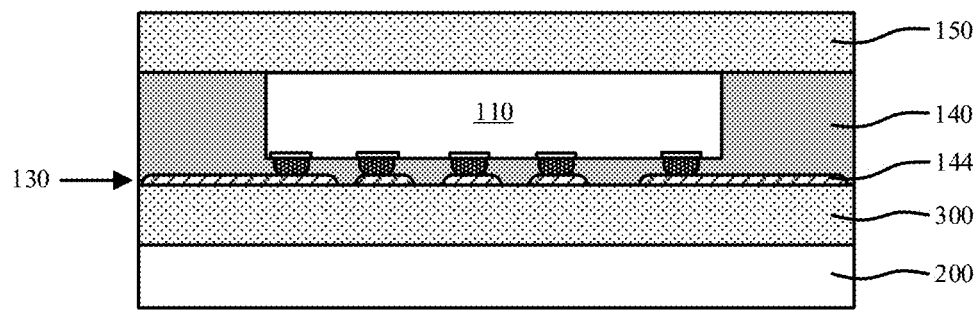
Figure 10F:
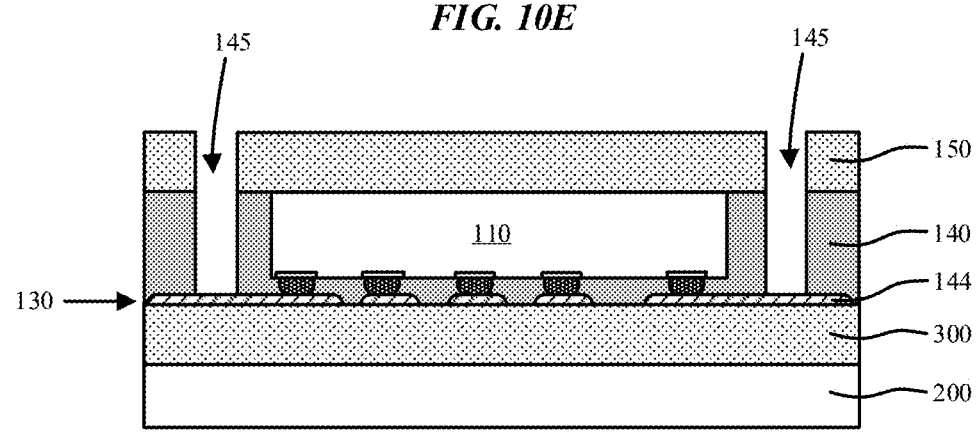
Figure 10G:
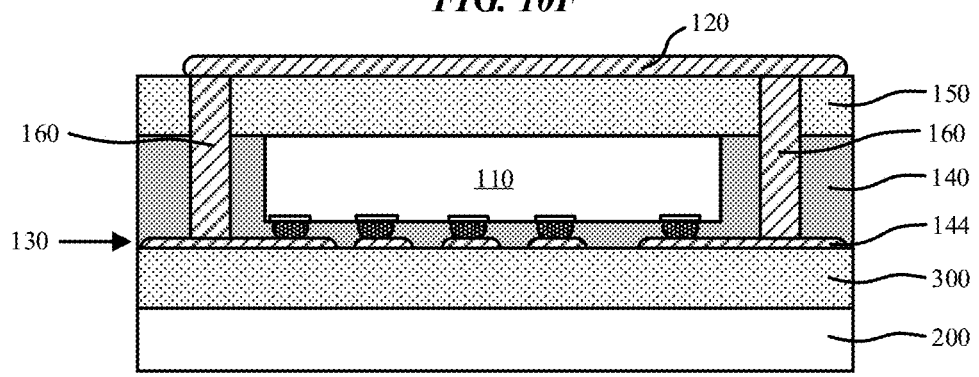
Figure 10H:
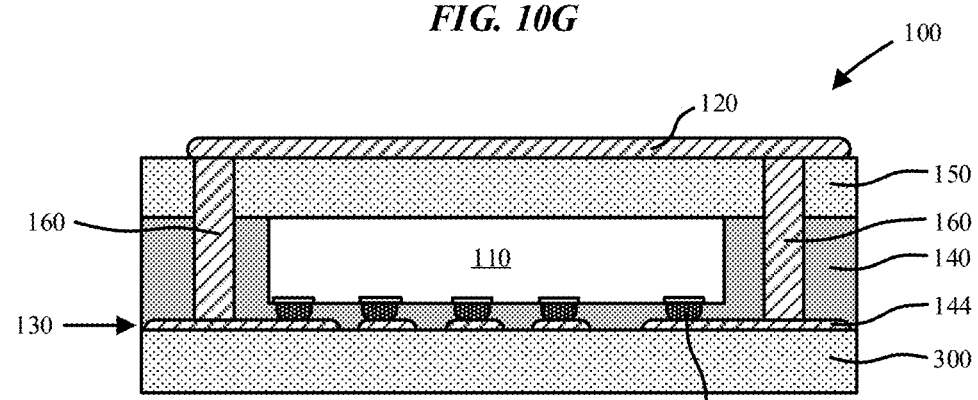

Referring to FIGS. 10C-10D, in either order, at operation 9020 an insulating layer is formed on the routing layer 130, and at operation 9030 a chip 110 is mounted on the routing layer 130. In the particular sequence illustrated the insulating layer 140 can be formed prior to mounting the chip 110, though the order can be reversed. Insulating layer 140 may be formed of any materials previously described for the insulating layer 140 and may be deposited using a suitable technique such as spraying or other coating technique. In such a sequence, the chip 110 can be mounted prior to curing the insulating layer 140. Alternatively, a cavity can be etched into the insulating layer 140 prior placement of the chip 110. In yet another embodiment, the chip 110 can be mounted prior to formation of the insulating layer 140.

The processing sequence illustrated in FIGS. 10E-10H may then proceed similarly as that illustrated and described with regard to FIGS. 7D-7G. In particular, a top side passivation layer 150 can be formed, followed by formation of via openings 145 through the insulating layer 140 (and top side passivation layer 150 if present) to expose the routing layer 130, or specifically wiring layer 144. Either sequentially or simultaneously, the electrically conductive through vias 160 are formed within the via openings 145 and the electrically conductive sensor pattern 120 are formed at operations 9040 and 9050.

Figure 11:
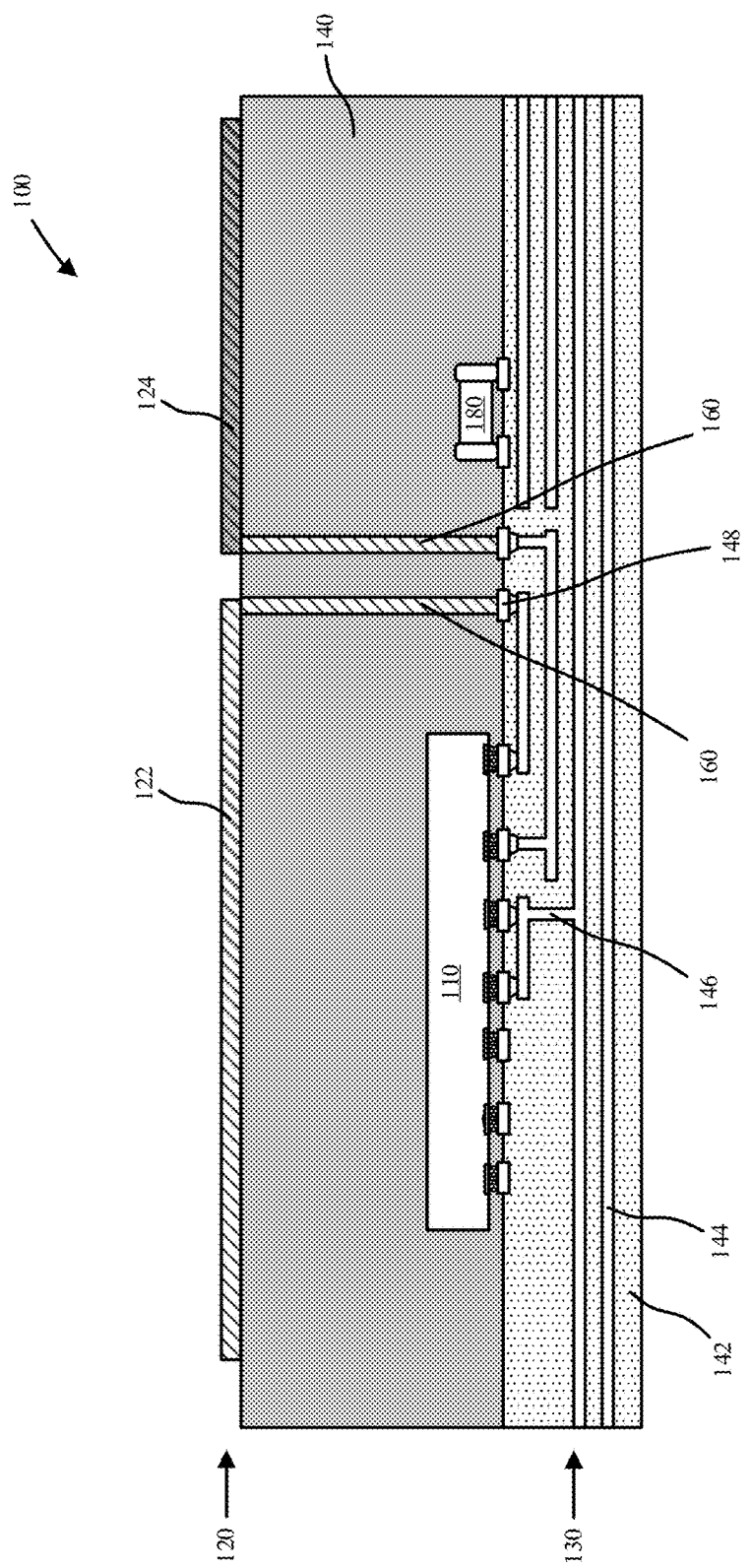
FIG. 11 is a cross-sectional side view illustration of a temperature sensor package with embedded chip and back side electrically conductive sensor pattern in accordance with an embodiment.

FIG. 11 is a cross-sectional side view illustration of a temperature sensor package 100 with embedded chip 110 and back side electrically conductive sensor pattern 120 in accordance with an embodiment. In particular, FIG. 11 shares many structural similarities to the embodiment illustrated and described with regard to FIG. 2, with one variation being that the temperature sensor package 100 of FIG. 11 can be fabricated using laser direct structuring (LDS). In an embodiment, the insulating layer 140 is an LDS compatible material including a dispersed non-conductive metal organic compound, and the electrically conductive through vias 160 may be defined using LDS. Specifically, the plurality of through vias 160 can include a nucleation layer of metal particles of the metal in the dispersed non-conductive metal organic compound. Similarly, the electrically conductive sensor pattern 120 can include a nucleation layer pattern of metal particles of the metal in the dispersed non-conductive metal organic compound.

Figure 12:
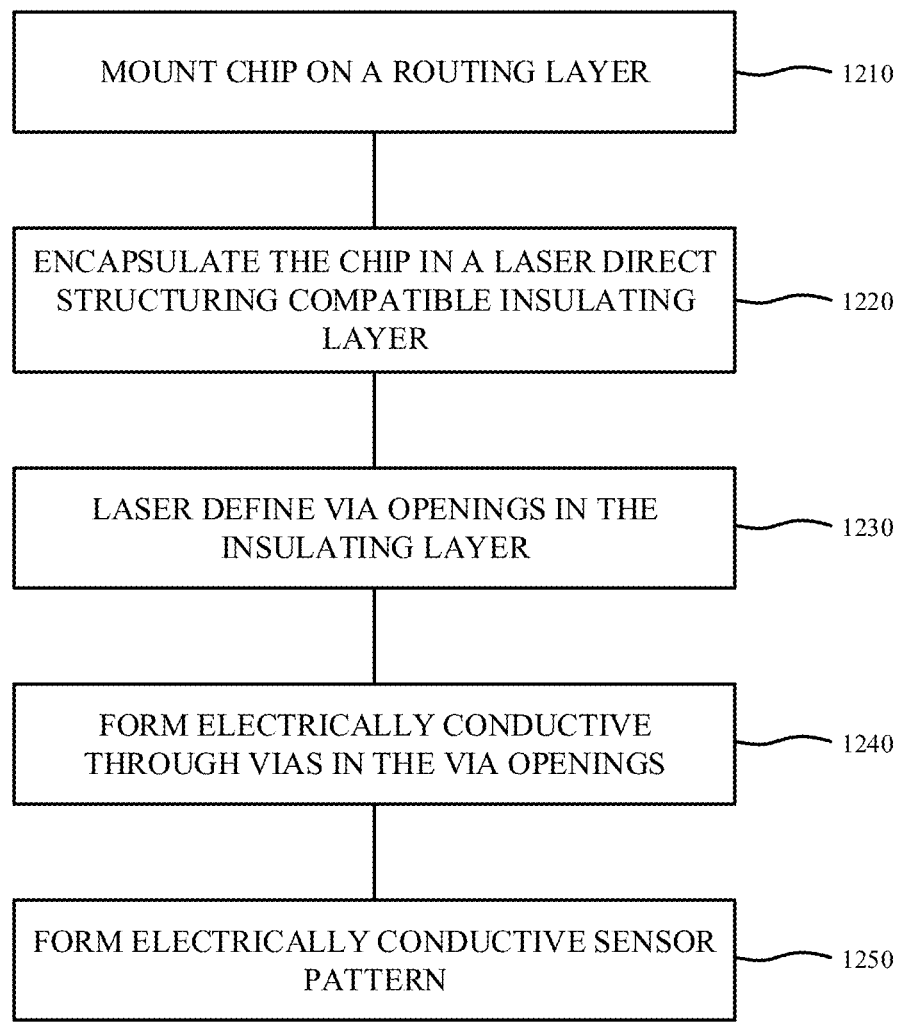
FIG. 12 is a flow diagram of a method of fabricating the temperature sensor package of FIG. 11 in accordance with an embodiment.

FIG. 12 is a flow diagram of a method of fabricating the temperature sensor package of FIG. 11 in accordance with an embodiment. FIGS. 13A-13E are schematic cross-sectional side view illustrations of a method of fabricating the temperature sensor package of FIG. 11 in accordance with an embodiment. In interest of clarity and conciseness the processing sequences of FIGS. 12 and 13A-13D are described concurrently.

Figure 13A:
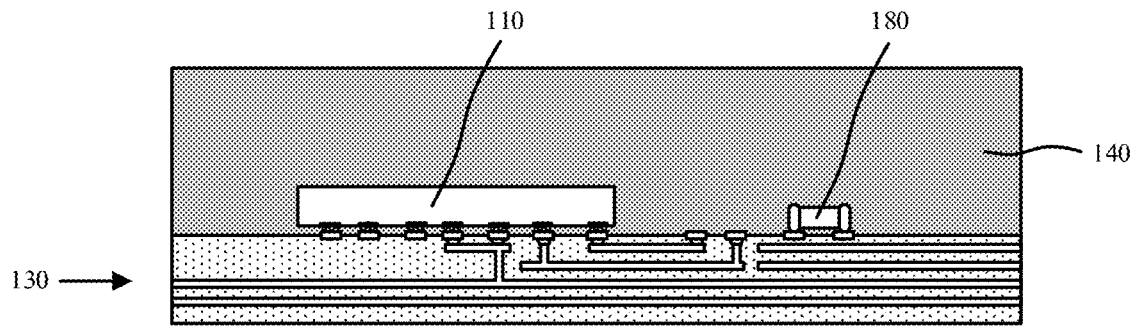
FIGS. 13A-13E are schematic cross-sectional side view illustrations of a method of fabricating the temperature sensor package of FIG. 11 in accordance with an embodiment.
Figure 13B:
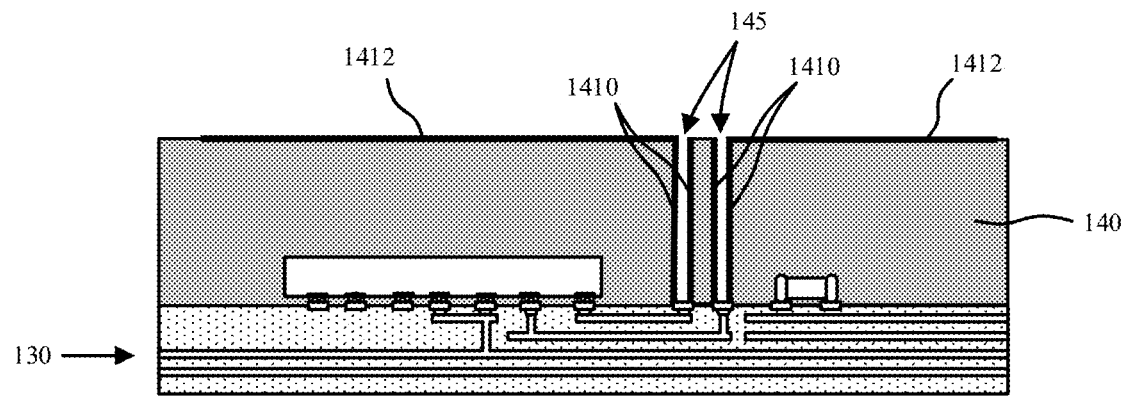
Figure 13C:
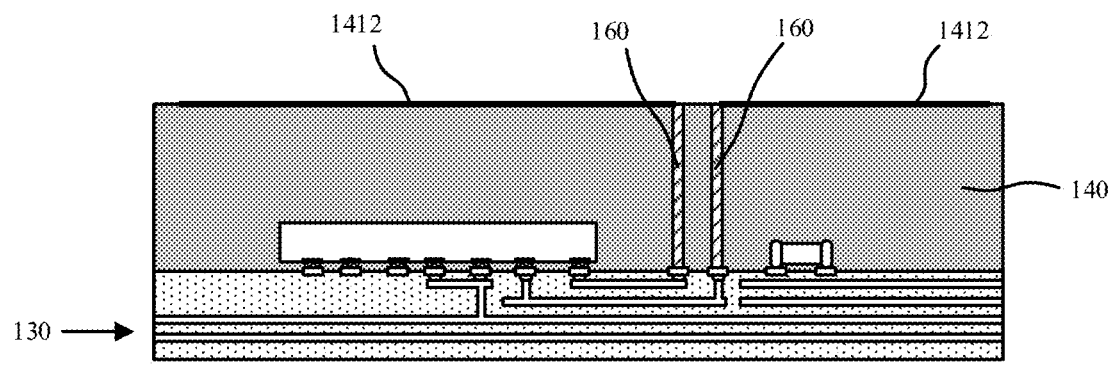

Referring now to FIG. 13A, at operation 1210 a chip 110 is mounted onto the routing layer 130. It is to be appreciated that additional components 180 can also be similarly mounted in all embodiments described herein. For example, one or more components 180 may be passive devices such as capacitors, etc. used for chip 110 (e.g. digital IC). In an embodiment, routing layer 130 is a printed circuit board (PCB), which may optionally be a rigid substrate. The chip 110 and optional component(s) 180 are then encapsulated in an insulating layer 140 at operation 1220. In accordance with embodiments, the insulating layer 140 may be an LDS compatible material. It is to be appreciated that while components 180 are only described and illustrated with regard to the embodiment of FIG. 12 that the components 180 can be similarly integrated adjacent the chips 110 in all other embodiments described herein.

LDS compatible molding compounds in accordance with embodiments may include a matrix material, and an LDS additive dispersed in the matrix material. For example, the LDS additive may be a non-conductive metal organic compound. This may include a variety of metal oxide compositions, which may be compounded with (e.g. complexed) with the matrix material (e.g. resin). In an exemplary embodiment, the LDS additive is a dispersed tin oxide composition that is complexed with the matrix material. Embodiments are not limited to tin oxide, and a variety of other non-conductive metal organic compounds may be used, including other compounded metal oxides.

A variety of organic materials can be used for the matrix material, which may be dependent upon temperature exposure. Low temperatures materials include polycarbonate (PC) and acrilonitrile butadiene styrene (ABS). Medium temperature material that can withstand soldering temperatures include polycaprolactam (PA6/6) and polyphthalamides (PPA). A higher temperature material that can withstand virtually any soldering polyether ether ketone (PEEK). Other suitable material may include polypropylene (PP), polyethylene terpthalate (PET), polybutylene terpthalate (PBT), polyphenylene sulfide (PPS), and liquid crystal polymers (LCP).

At operation 1230 the via openings 145 are laser defined in the insulating layer 140. The LDS additive, and laser parameters are selected so that upon application of the laser to the molding compound, the elemental metal in the non-conductive metal organic compound breaks from the compound and forms nucleation particles within a nucleation layer 1410 forming a conducting path corresponding to the laser pattern. As shown, the nucleation layer 1410 may line the sidewalls of the via openings 145. Optionally, the laser process may be applied to the top surface 143 of the insulating layer 140 to additionally define nucleation layers 1412 that can subsequently be used to form the electrically conductive sensor pattern.

Figure 13D:
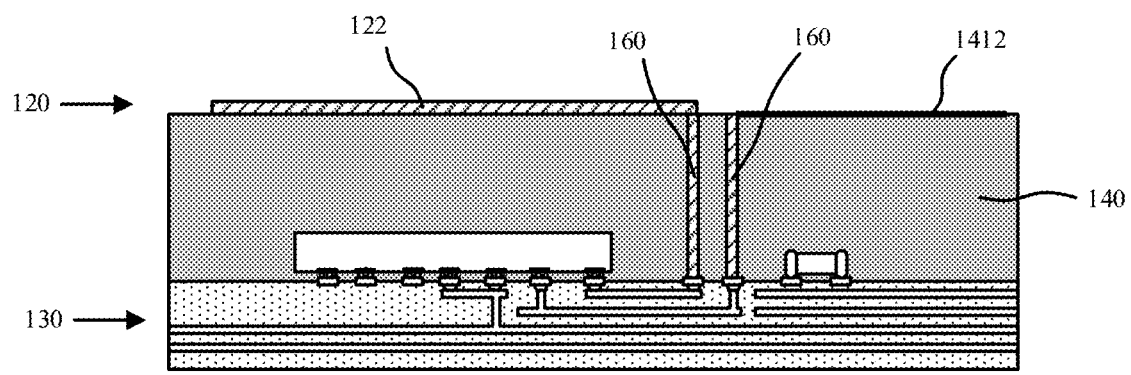
Figure 13E:
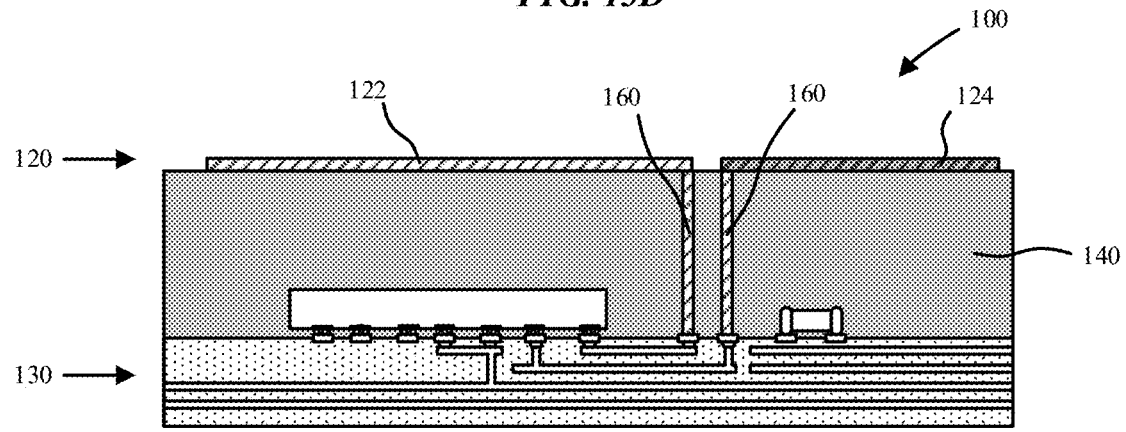
Figure 14:
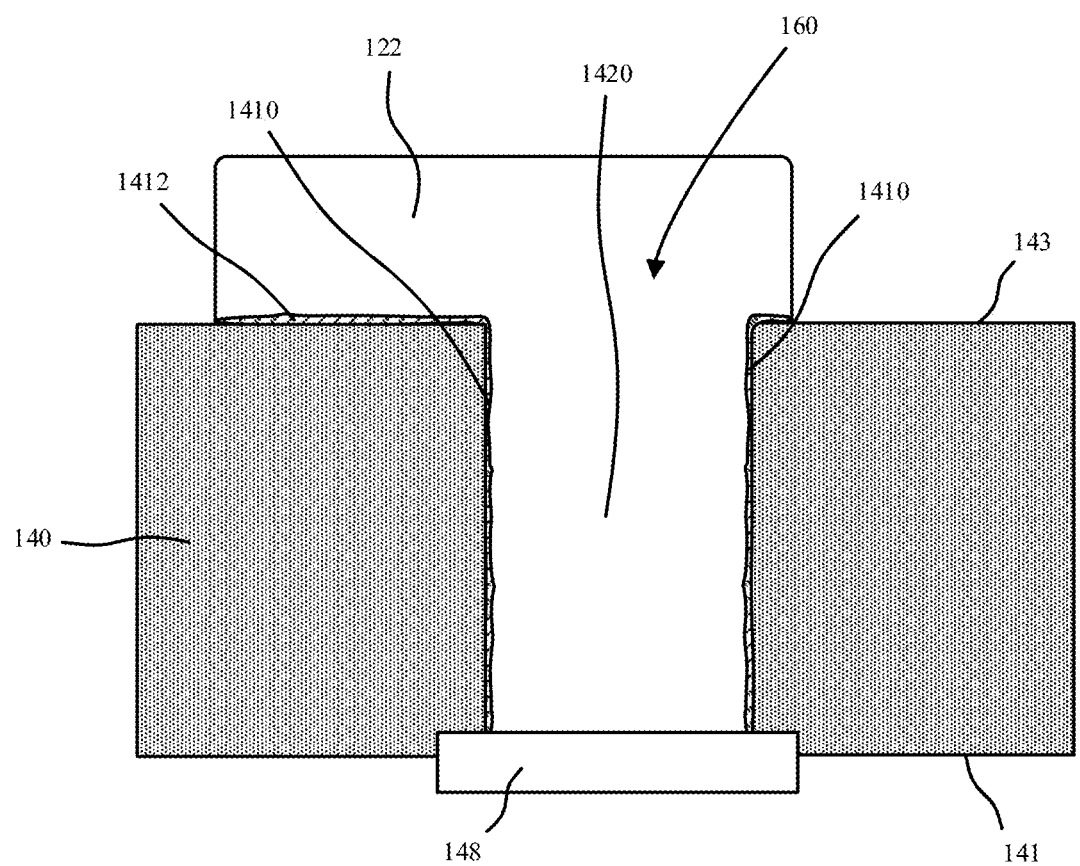
FIG. 14 is a close-up schematic cross-sectional side view illustration of a through via and electrically conductive sensor pattern layer formed using laser direct structuring (LDS) and plating in accordance with an embodiment.

In accordance with embodiments, the through vias 160 can be created by laser followed by filling the via openings 145 formed by the laser process at operation 1240 by plating or dispensing of a conductive paste (e.g. silver-based epoxy) as a bulk layer 1420 into the blanked via openings 145. The electrically conductive sensor pattern 120 may then be formed on the insulating layer at operation 1250. As previously described, the electrically conductive sensor pattern 120 may be formed of the same or different materials than the through vias 160, and may be formed sequentially or simultaneously. In an embodiment, the electrically conductive sensor pattern 120 is an RTD pattern of same composition (e.g. single metal layer, or metal stack). In an embodiment, the electrically conductive sensor pattern 120 is a thermocouple pattern including dissimilar metallic layers 122, 124. FIGS. 13D-13E illustrate such a processing sequence. In an embodiment, the electrically conductive sensor pattern 120 is formed using a screen printing, dispensing or selective plating technique. In an embodiment, the nucleation (seed) layers 1412 can be utilized for a plating sequence for the formation of layers 122, 124. Thus, nucleation (seed) layers 1412 may be formed of a same material, for dissimilar layers 122, 124. Various metal layers can be formed with the plating process including gold, nickel, silver, zinc, tin, platinum, platinum-rhodium alloy, iron, iron-copper alloy, copper-nickel alloy, etc. FIG. 14 is a close-up schematic cross-sectional side view illustration of a through via 160 and electrically conductive sensor pattern 120 and layer 122 formed using LDS and plating in accordance with an embodiment.

Figure 15:
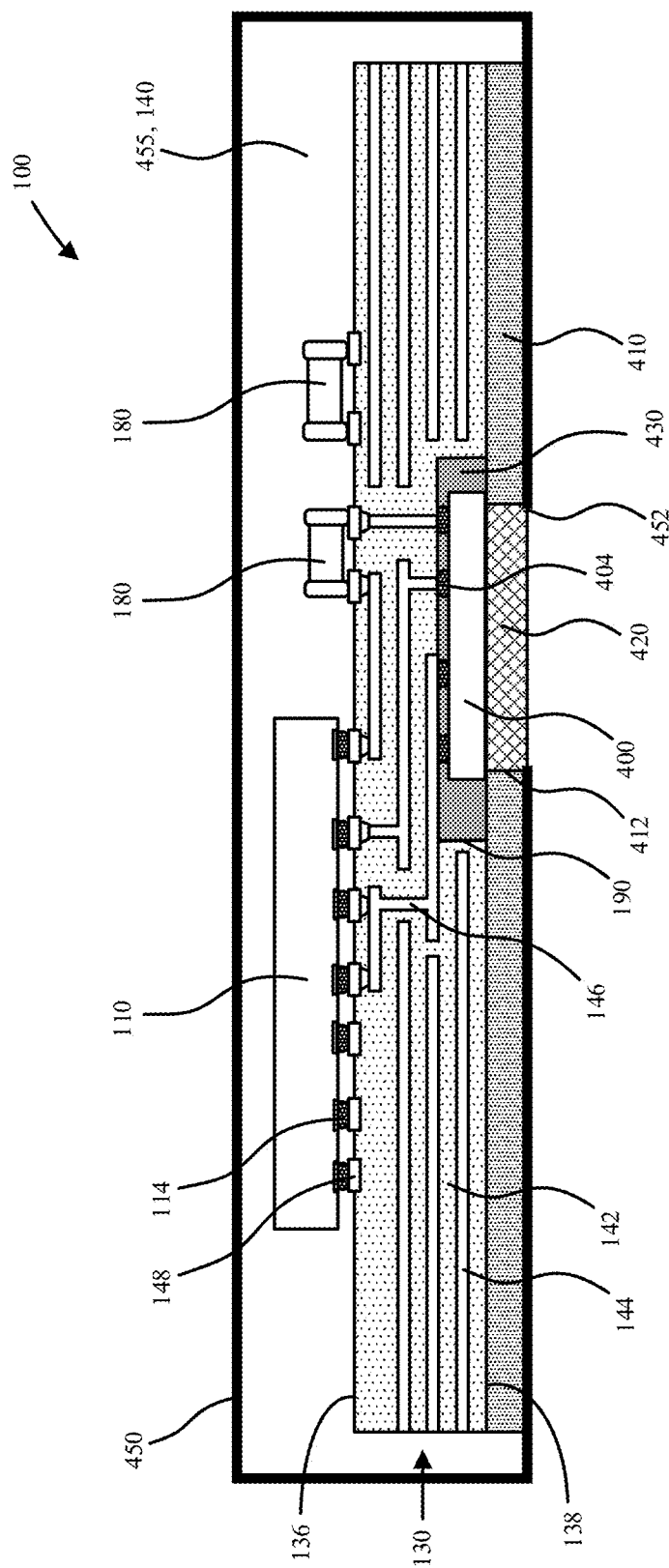
FIG. 15 a cross-sectional side view illustration of a temperature sensor package with embedded transducer for non-contact temperature sensing in accordance with an embodiment.

Up until this point, the described embodiments have been directed to touch-sensitive temperature sensor packages 100 where the electrically conductive sensor pattern 120 can form a portion of the sensing surface for the package. FIG. 15 a cross-sectional side view illustration of a temperature sensor package with embedded transducer for non-contact temperature sensing in accordance with an embodiment. In accordance with embodiments, embedding the transducer may provide save spacings. Additionally, short and flexible routing can be provided between the transducer and chip 110 for integration into different subsystems for non-contact temperature sensing.

In an embodiment, a temperature sensor package 100 includes a routing layer 130 (e.g. PCB) including a top side 136 and a bottom side 138, a cavity 190 formed in the bottom side 138 of the routing layer 130, and a transducer 400 mounted within the cavity 190. A chip 110 is mounted on the top side 136 of the routing layer and in electrical connection with the transducer (e.g. with routing layers 144, vias 146, etc.). An insulating layer 430 may encapsulate the transducer 400 within the cavity 190, optionally leaving a surface 401 exposed though this is not a strict requirement.

While not separately illustrated, an interposer (e.g. glass) or a low thermal conductive under-fill material can be used to provide thermal isolation between the chip 110 (e.g. digital IC) and the routing layer 130.

In an embodiment, the transducer 400 is an infrared (IR) sensor that measures temperature by receiving radiant heat from an object. For example, the transducer 400 may be a thermopile-based microelectromechanical systems (MEMS) IR sensor. Such sensors may be as small as a few hundred microns, and may additionally include a signal conditioner to convert an analog output from the thermopile into a digital input for the chip 110. The temperature sensor package 100 may additionally include an optical window 420 over a surface of the transducer. For example, the optical window 420 may be transparent to the IR wavelength, and optionally filter out other wavelength ranges to reduce noise. The optical window 420 may include multiple layers including a separate wavelength range filter layer. Alternatively, the transducer 400 may be designed to be responsive to another wavelength range (e.g. visible, etc.). Similarly, the optical window 420 may be designed to be transmissive to the operable wavelength range, and optionally filter out non-operable wavelengths.

The chip 110, routing layer 130, and thermal sensor arrangement may be secured inside an enclosure 450 in an embodiment. Enclosure 450 can be made of metal shield, glass, rigid plastic (like epoxy, polycarbonate, polyethylene), soft plastic (silicone, thermoplastic), etc. The enclosure can have on opening 452 in correspondence of the transducer 400, or such an opening 452 may not be needed when a material transparent to IR is used, like sapphire, silicon, fused silica, polycarbonate or acrylic. In an embodiment, the optical window 420 is arranged within an opening 412 in dielectric layer 410 formed on the bottom side 138 of the routing layer 130. The dielectric layer 410 may in turn be secured to the enclosure 450, with the optional opening 452 in the enclosure arranged over the optical window 420. In the illustrated embodiment, the chip and routing layer can be surrounded (including laterally surrounded) by an open space 455 within the enclosure 450. Alternatively, the open space 455 may be replaced with an insulating layer 140 that encapsulates the chip and routing layer. In an embodiment, insulating layer 140 is present without the enclosure 450.

In operation, the temperature sensor package 100 of FIG. 15 can be located at a working distance from a source, such as body skin of a target subject, allowing constant temperature monitoring. Physical contact between the source and temperature sensor package 100 is not required.

Figure 16:
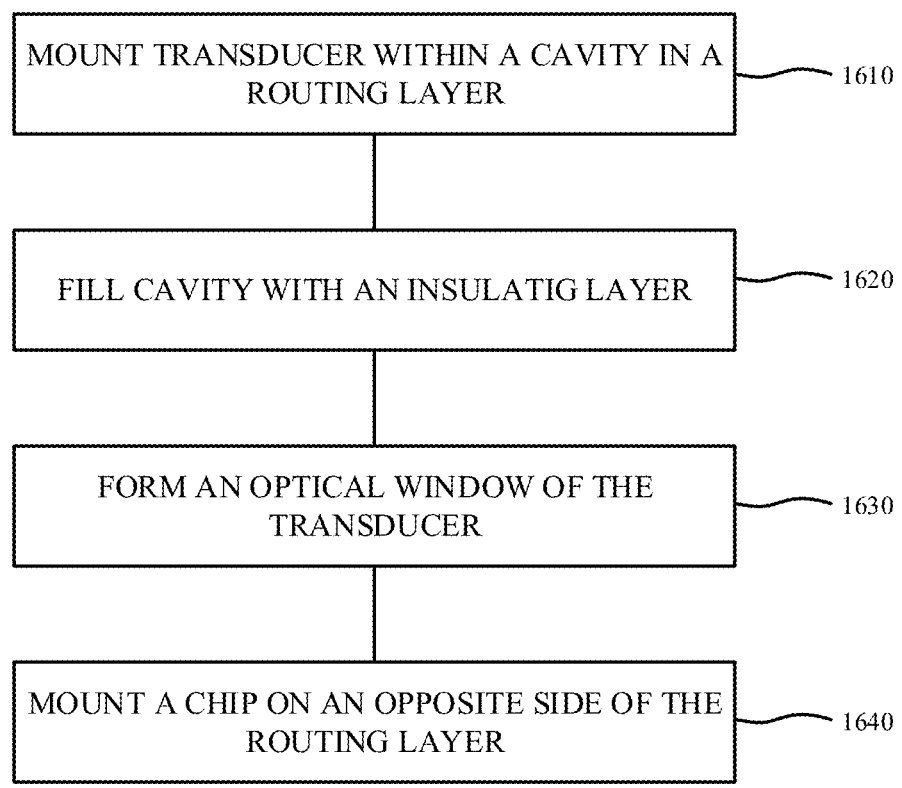
FIG. 16 is a flow diagram of a method of fabricating the temperature sensor package of FIG. 15 in accordance with an embodiment.
Figure 17A:
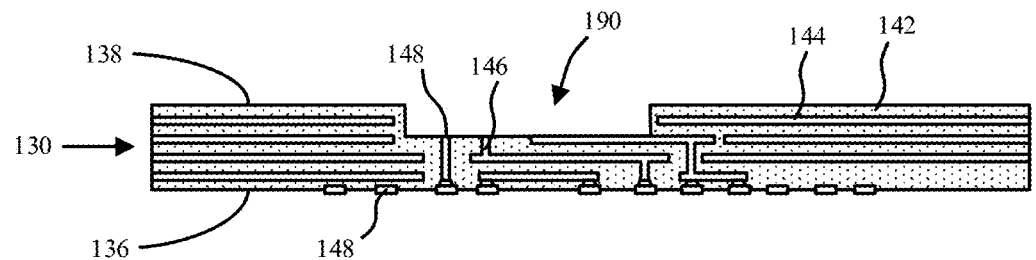
FIGS. 17A-17G are schematic cross-sectional side view illustrations of a method of fabricating the temperature sensor package of FIG. 15 in accordance with an embodiment.
Figure 17B:
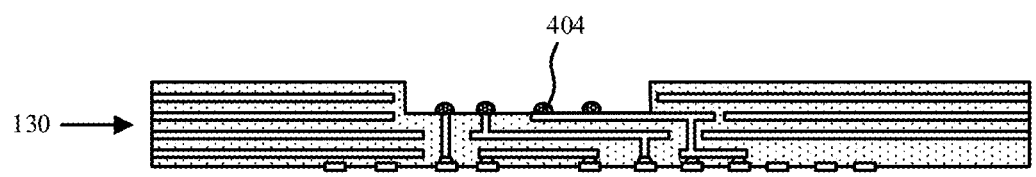
Figure 17C:
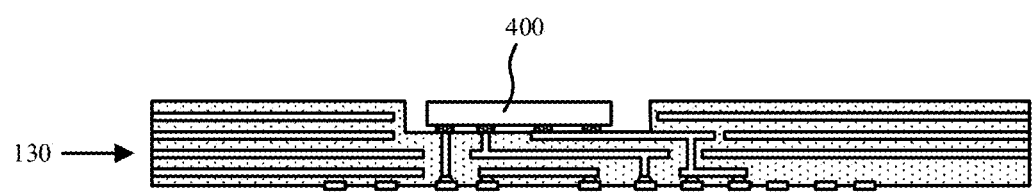

FIG. 16 is a flow diagram of a method of fabricating the temperature sensor package of FIG. 15 in accordance with an embodiment. FIGS. 17A-17G are schematic cross-sectional side view illustrations of a method of fabricating the temperature sensor package of FIG. 15 in accordance with an embodiment. At operation 1610 a transducer 400 is mounted within a cavity 190 formed in a routing layer 130. Routing layer 130 may be rigid (e.g. rigid PCB) or flexible substrate (e.g. flexible PCB, or redistribution layer formed using thing film processing). As shown in FIG. 17A-17C, the routing layer 130 may include one or more wiring layers 144, dielectric layers 142, and vias 146. Routing contacts 148 can be exposed on the top side 136, bottom side 138 and a mounting surface within cavity 190. Conductive bumps 404 (e.g. solder) can be applied to the routing contacts 148 within the cavity 190 followed by mounting of the transducer 400, or alternatively, conductive bumps 404 can be attached to the transducer 400 prior to mounting of the transducer 400 within the cavity 190. The transducer 400 can be also dipped in paste or flux prior to placement into the cavity to reduce manufacturing complexity.

Figure 17D:
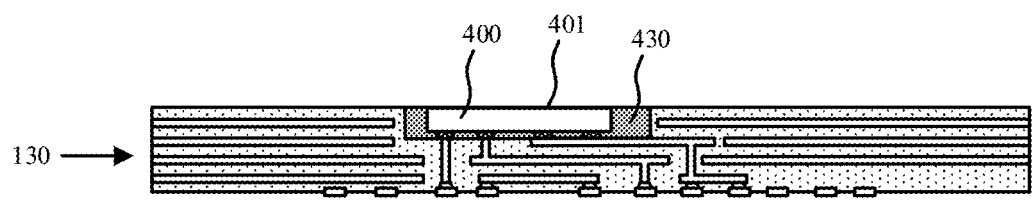
Figure 17E:
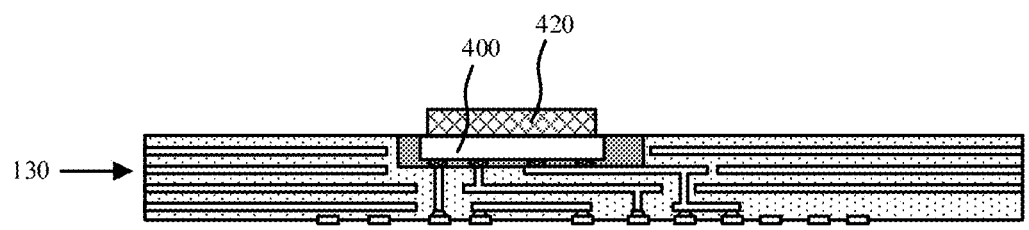
Figure 17F:
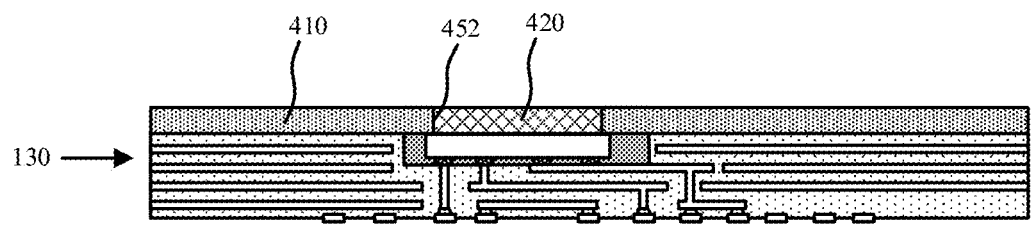
Figure 17G:
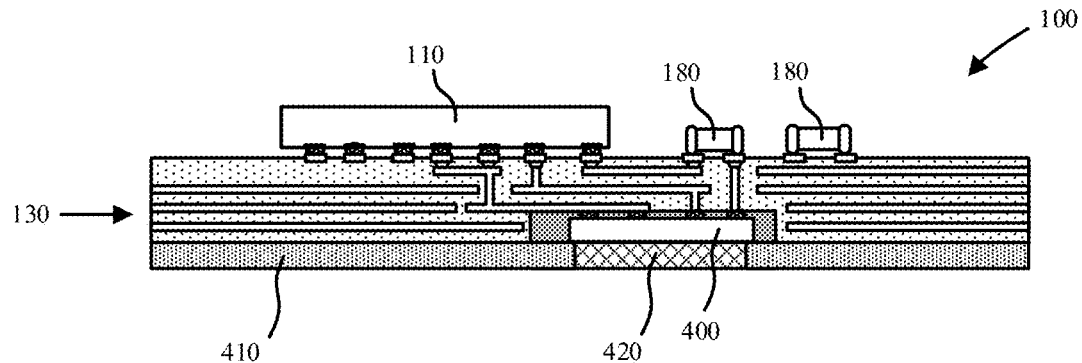

Referring now to FIG. 17D, at operation 1620 an insulating layer 430 is applied around the transducer 400 within the cavity 190 to encapsulate the transducer 400, optionally leaving a surface 401 exposed. An optical window 420 is then formed over the transducer 400 at operation 1630. As shown in FIG. 17E-17F, formation of the optical window may include forming a layer of the optical window 420 (which can include a single layer, or stack of multiple layers), followed by formation of a dielectric layer (coating) 410 around the optical window 420. Additional components can the be mounted on the opposite side (e.g. top side) of the routing layer 130 at operation 1640 as shown in FIG. 17G. This may be followed by integration of an enclosure or additional encapsulation/molding to form the package illustrated in FIG. 15.

In the following description of FIGS. 18 and 21, temperature sensor package 100 variations are described and illustrated that share similar features to that of the embodiment described an illustrated with regard to FIG. 1 such as a routing layer 130 that includes a chip contact area 132 and a touch area 134 adjacent to the chip contact area 132. Referring now to the embodiment illustrated in FIG. 18, the routing layer 130 may include a rigid-flex connection 1800, in which the chip 110 is mounted on the rigid portion 1810 of the rigid-flex connection and the electrically conductive sensor pattern 120 spans over flexible portion 1820 of the rigid-flex connection. Similar to previous descriptions of the routing layers 130, the rigid flex connection 1800 may include one or more dielectric layers 142 and wiring layers 144. The rigid portion 1810 may include different dielectric layers than the flexible portion 1820 and/or additional layers such as glass cloth, etc. to provide rigidity. As shown, a top side metallization layer(s) may be used to form both a top side wiring layer 144 and electrically conductive sensor pattern 120 on a top side of the rigid-flex connection 1800.

Figure 18:
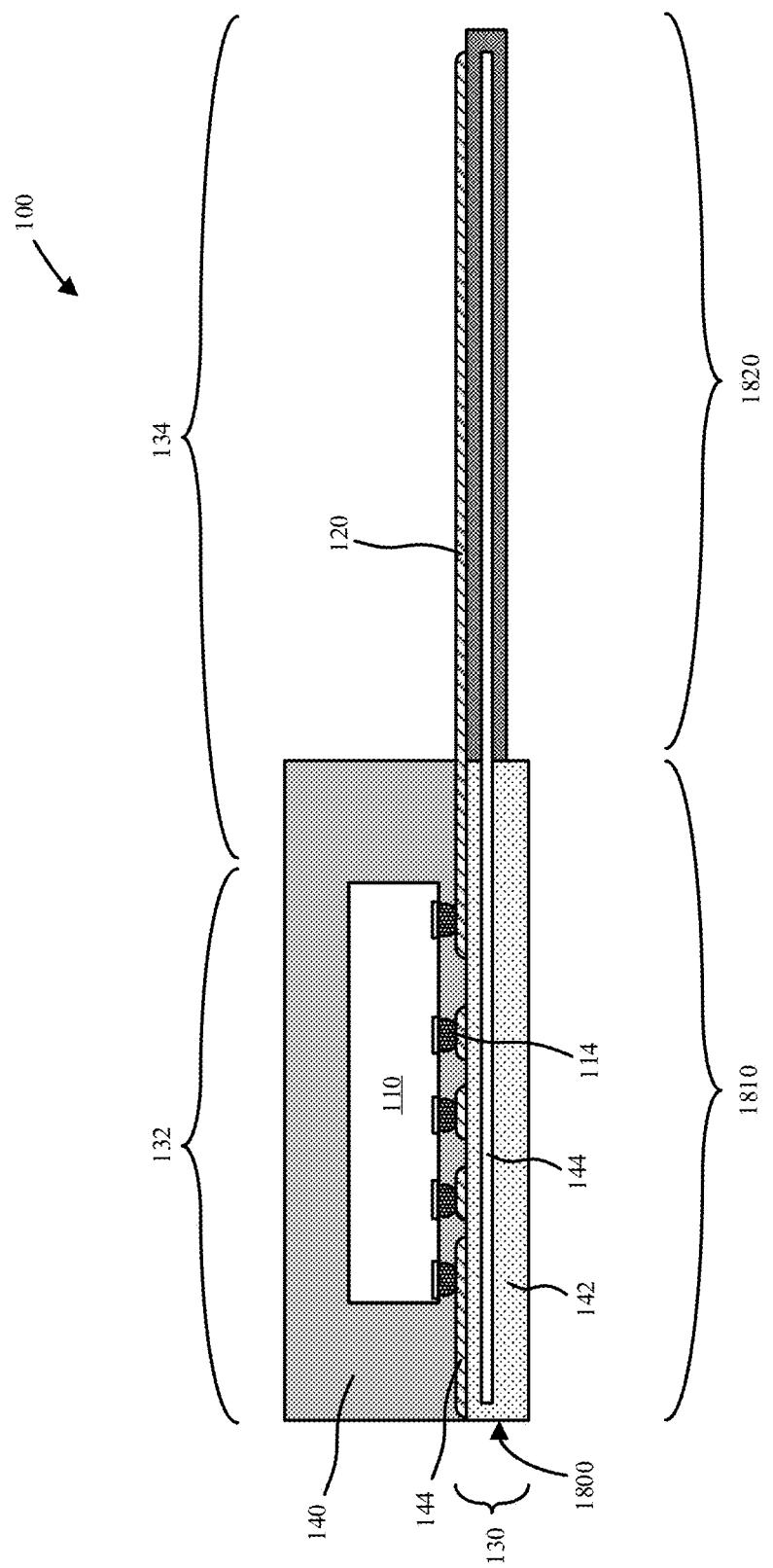
FIG. 18 a cross-sectional side view illustration of a temperature sensor package with a chip mounted on a rigid-flex connection in accordance with an embodiment.
Figure 19:
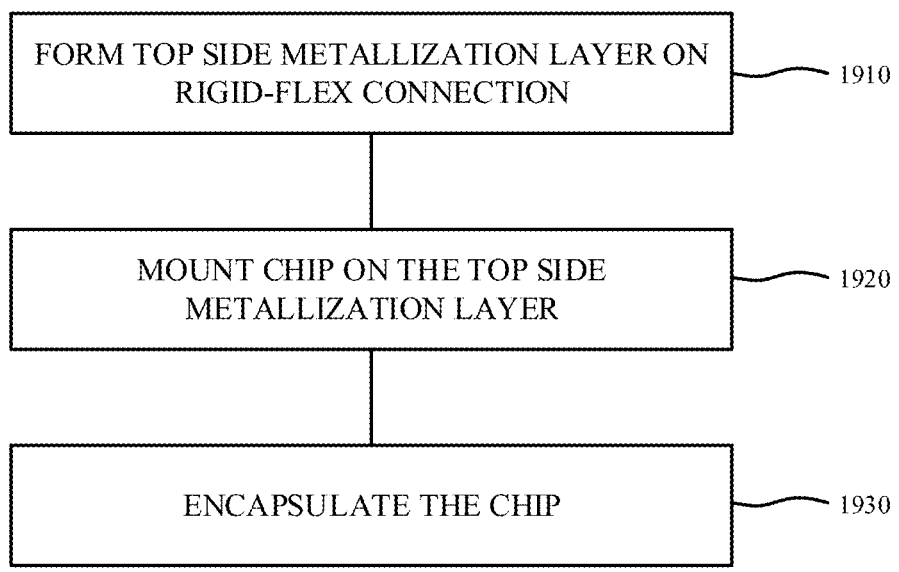
FIG. 19 is a flow diagram of a method of fabricating the temperature sensor package of FIG. 18 in accordance with an embodiment.
Figure 20A:
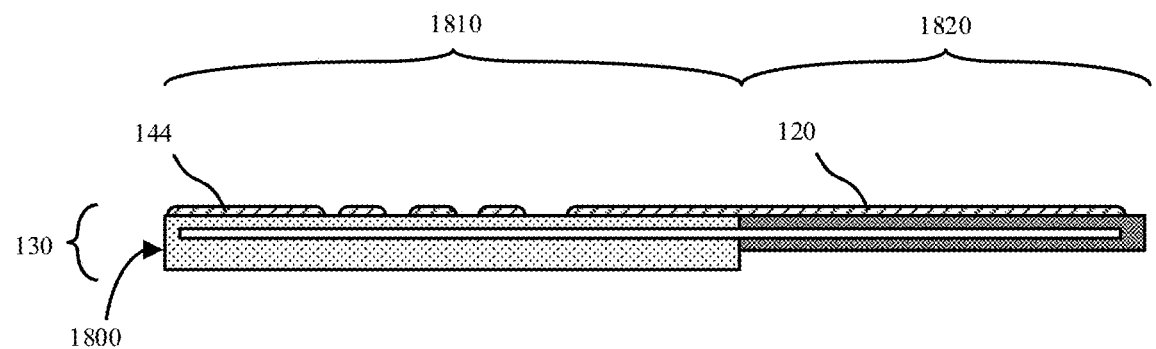
FIGS. 20A-20C are schematic cross-sectional side view illustrations of a method of fabricating the temperature sensor package of FIG. 18 in accordance with an embodiment.
Figure 20B:
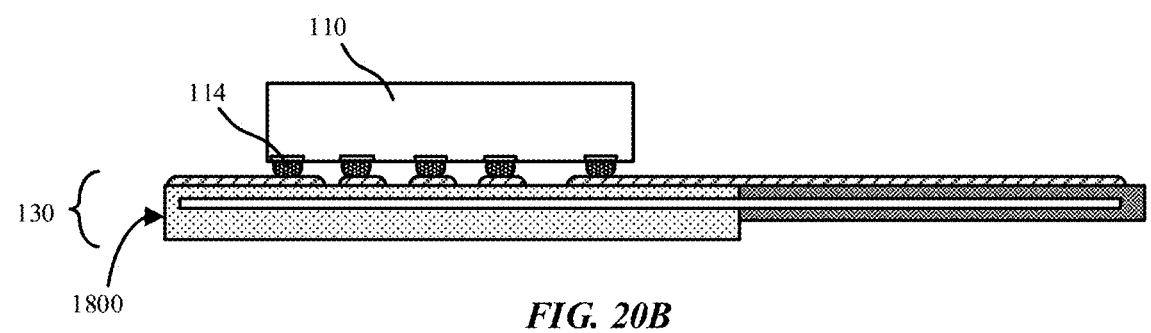
Figure 20C:
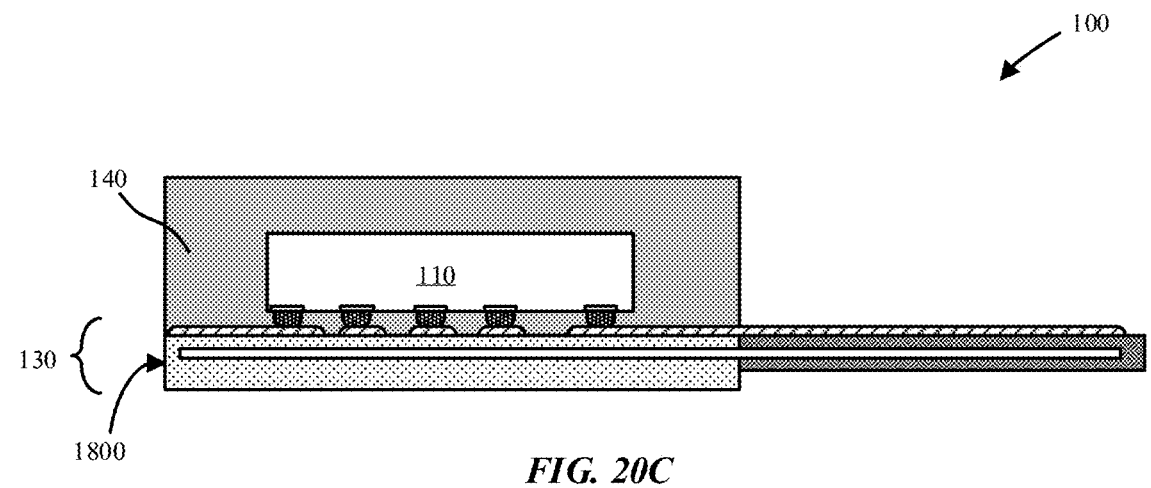

FIG. 19 is a flow diagram of a method of fabricating the temperature sensor package of FIG. 18 in accordance with an embodiment. FIGS. 20A-20C are schematic cross-sectional side view illustrations of a method of fabricating the temperature sensor package of FIG. 18 in accordance with an embodiment. In interest of clarity and conciseness the processing sequences of FIGS. 19 and 20A-20C are described concurrently. At operation 1910 a top side metallization layer including a wiring layer 144 and electrically conductive sensor pattern 120 is formed on a rigid-flex connection 1800. The top side metallization layer may be formed using any suitable technique, such as plating (electroplating, electroless plating), printing, dispensing, etc. As shown in FIG. 20A the top side metallization layer spans both the rigid portion 1810 and flexible portion 1820 of the rigid-flex connection 1800. At operation 1920 a chip 110 is then mounted onto the top side metallization layer on the rigid portion 1810 as shown in FIG. 20B, followed by encapsulation with an insulating layer 140 at operation 1930 as shown in FIG. 20C.

Figure 21:
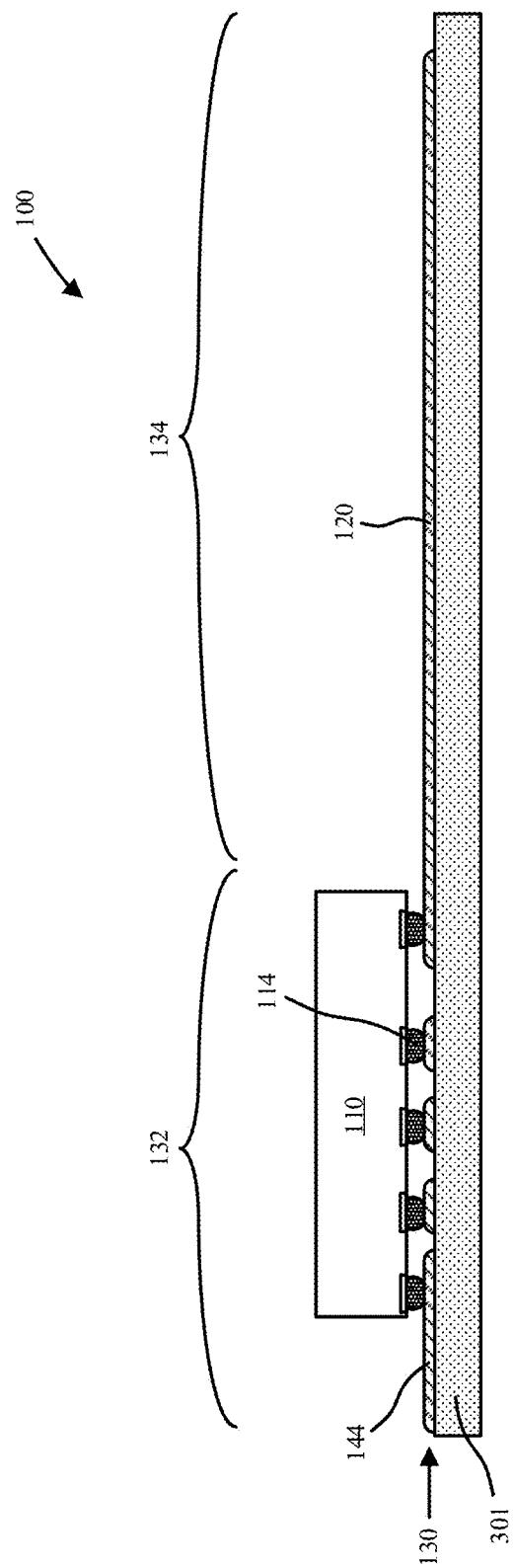
FIG. 21 a cross-sectional side view illustration of a flexible temperature sensor package in accordance with an embodiment.

Referring now to the embodiment illustrated in FIG. 21, the routing layer 130 may be formed on a single substrate 301. For example, substrate 301 may be a flexible insulating material, such as an electrical grade polymer such as polyimide. Routing layer 130 may be a top side metallization layer(s) including both wiring layer 144 and the electrically conductive sensor pattern 120. The top side metallization layer may be formed using any suitable technique, such as plating (electroplating, electroless plating), printing, dispensing, etc.

Figure 22:
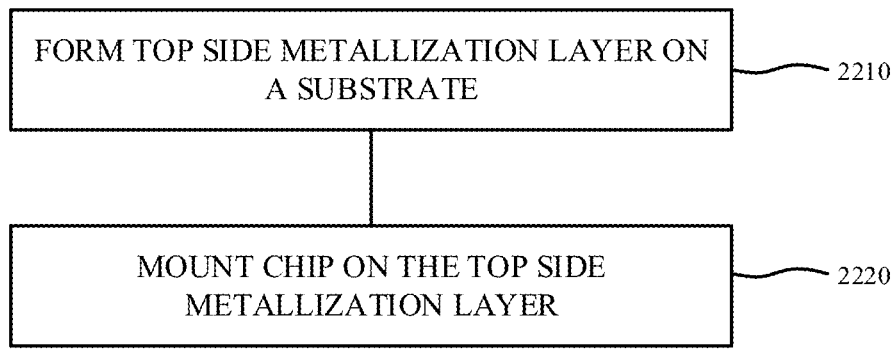
FIG. 22 is a flow diagram of a method of fabricating the temperature sensor package of FIG. 21 in accordance with an embodiment.
Figure 23A:
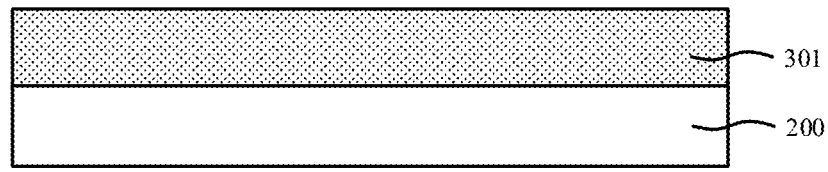
FIGS. 23A-23D are schematic cross-sectional side view illustrations of a method of fabricating the temperature sensor package of FIG. 21 in accordance with an embodiment.
Figure 23B:
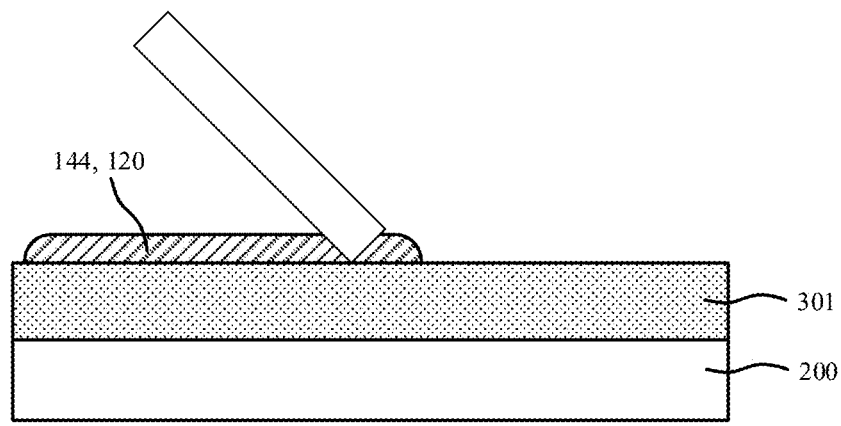
Figure 23C:
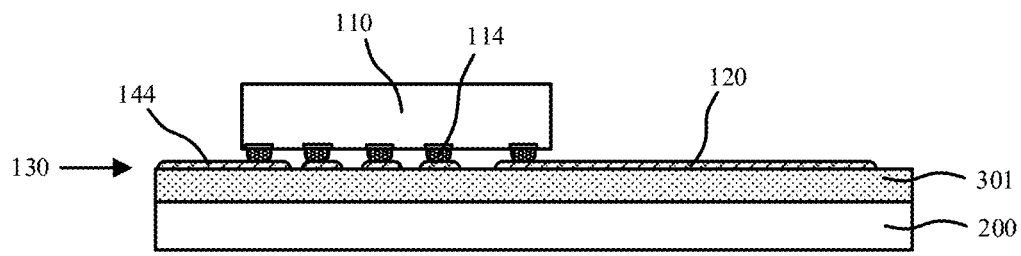
Figure 23D:
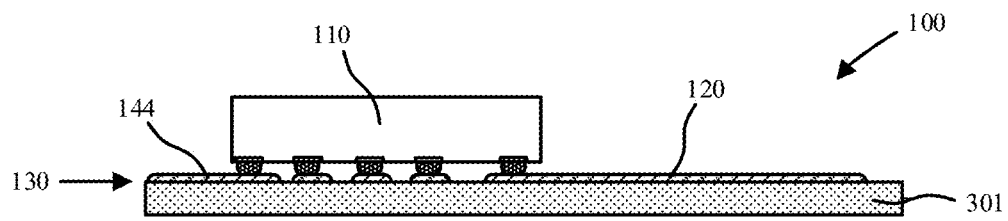

FIG. 22 is a flow diagram of a method of fabricating the temperature sensor package of FIG. 21 in accordance with an embodiment. FIGS. 23A-23D are schematic cross-sectional side view illustrations of a method of fabricating the temperature sensor package of FIG. 21 in accordance with an embodiment. In interest of clarity and conciseness the processing sequences of FIGS. 22 and 23A-23D are described concurrently. At operation 2210 a top side metallization layer including a wiring layer 144 and electrically conductive sensor pattern 120 is formed on the substrate 301. The top side metallization layer may be formed using any suitable technique, such as plating (electroplating, electroless plating), printing, dispensing, etc. As shown in FIGS. 23A-3B, the substrate 301 may first be formed onto a rigid carrier substrate. For example, this may be accomplished by lamination, deposition, dispensing, etc. The top side metallization layer is then formed using a variety of techniques such as screen printing or other dispensing method, physical or chemical vapor deposition, and plating. Screen printing or other dispensing methods in particular may be particularly simple for manufacturing. The chip 110 is then mounted onto the wiring layer 144 at operation 2220 as shown in FIG. 23C, followed by removal of the rigid carrier substrate 200 as shown in FIG. 23D.

Figure 24:
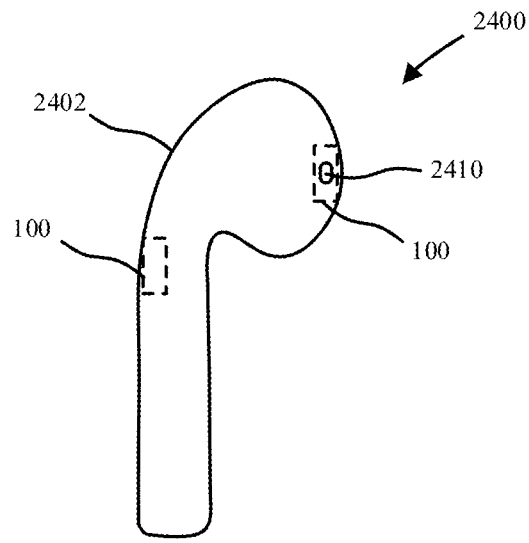
FIGS. 24-25 are schematic side view illustrations of earbuds in accordance with embodiments.
Figure 25:
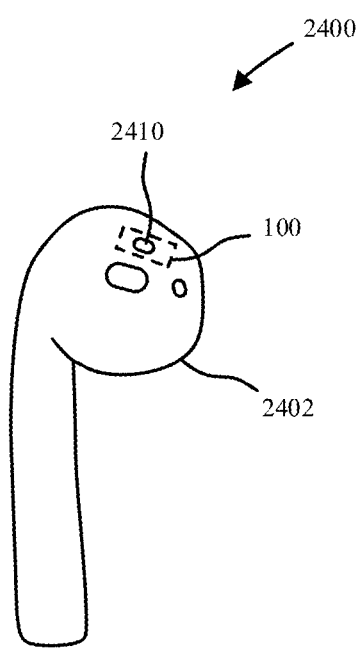
Figure 26:
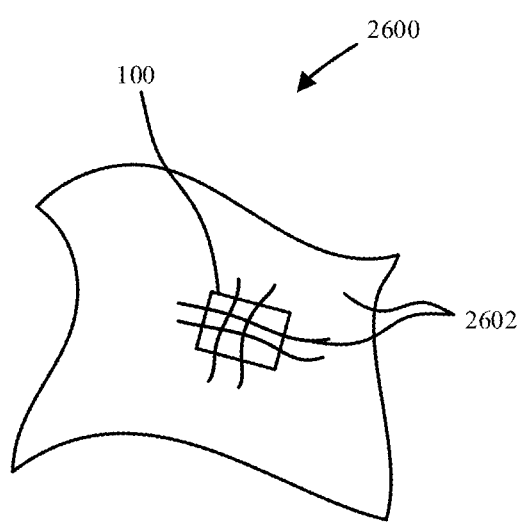
FIG. 26 are schematic side view illustrations of a wearable device in accordance with an embodiment.

FIGS. 24-26 illustrate various wearable health devices in which the various embodiments can be implemented. These illustrations are intended to be exemplary and non-exhaustive implementations. FIGS. 24-25 are schematic side view illustrations of portable electronic devices such as earbuds 2400 in accordance with embodiments that include a housing 2402 and one or more temperature sensor packages 100 described herein. For example, an IR temperature sensor package 100 such as that described and illustrated with regard to FIG. 15 can be aligned with an opening 2410 in the housing for non-contact temperature sensing. Specifically, the optical window 420 may aligned with opening 2410. In other configurations, any of the touch sensitive temperature sensor packages 100 described herein can be arranged within, on, or aligned with a surface of the housing 2402 for touch sensing. FIG. 26 is a schematic side view illustration of a wearable device 2600 in which a temperature sensor package 100 secured within a fabric 2602. For example, the fabric can be integrated into a piece of clothing such as shirt, headband, glove, strap, etc.

In utilizing the various aspects of the embodiments, it would become apparent to one skilled in the art that combinations or variations of the above embodiments are possible for forming temperature sensor packages. Although the embodiments have been described in language specific to structural features and/or methodological acts, it is to be understood that the appended claims are not necessarily limited to the specific features or acts described. The specific features and acts disclosed are instead to be understood as embodiments of the claims useful for illustration.

What is claimed is:

1. A temperature sensor package comprising:
 a routing layer;
 a chip mounted face down on the routing layer;
 an insulating layer encapsulating the chip on the routing layer;
 a plurality of through vias through the insulating layer; and
 an electrically conductive sensor pattern over the insulating layer and coupled to the plurality of through vias;
 wherein at least a portion of the electrically conductive temperature sensor pattern and at least one of the plurality of through vias is formed of a same material comprising coalesced metallic particles.

2. The temperature sensor package of claim 1, wherein the electrically conductive sensor pattern is directly over a back side of the chip.

3. The temperature sensor package of claim 1, wherein the chip is solder bonded to the routing layer.

4. The temperature sensor package of claim 1, secured within a portable electronic device.

5. The temperature sensor package of claim 1, secured to a fabric of a wearable device.

6. A temperature sensor package comprising:
 a routing layer;
 a chip mounted face down on the routing layer;
 an insulating layer encapsulating the chip on the routing layer;
 a plurality of through vias through the insulating layer;
 an electrically conductive sensor pattern over the insulating layer and coupled to the plurality of through vias;
 wherein the insulating layer is a laser direct structuring (LDS) compatible material including a dispersed nonconductive metal organic compound; and
 wherein the plurality of vias include a nucleation layer of metal particles of the metal in the dispersed nonconductive metal organic compound.

7. The temperature sensor package of claim 6, wherein the electrically conductive sensor pattern includes a nucleation layer pattern of metal particles of the metal in the dispersed non-conductive metal organic compound.

8. The temperature sensor package of claim 6, wherein the electrically conductive sensor pattern is a thermocouple pattern including a first pattern of a first conductive material and a second pattern of a second conductive material different from the first conductive material.

9. The temperature sensor package of claim 8, wherein the plurality of through vias includes a first via connected to the first pattern, and a second via connected to the second pattern.

10. The temperature sensor package of claim 9, wherein the first via comprises the first conductive material, and the second via comprises the second conductive material.

11. The temperature sensor package of claim 6, wherein the electrically conductive sensor pattern is a resistance temperature detector (RTD) pattern.

12. A temperature sensor package comprising:
a routing layer;
a chip mounted face down on the routing layer;
an insulating layer encapsulating the chip on the routing layer;
a plurality of through vias through the insulating layer;
an electrically conductive sensor pattern over the insulating layer and coupled to the plurality of through vias;
wherein the electrically conductive sensor pattern is a resistance temperature detector (RTD) pattern formed of a different material than the plurality of through vias.

13. The temperature sensor package of claim 12, secured within a portable electronic device.

14. The temperature sensor package of claim 12, secured to a fabric of a wearable device.

15. A temperature sensor package comprising:
a routing layer including:
a chip contact area; and
a touch area adjacent the chip contact area, the touch area including an electrically conductive sensor pattern electrically connected to the chip contact area; and
a chip bonded to the routing layer in the chip contact area;
wherein the chip is encapsulated in an insulating layer laterally surrounding the chip on a top side of the routing layer, wherein the insulating layer spans the touch area.

16. The temperature sensor package of claim 15, secured within a portable electronic device.

17. The temperature sensor package of claim 15, wherein the chip is mounted on a first side of the routing layer, and a second side of the routing layer opposite the first side includes the electrically conductive sensor pattern.

18. The temperature sensor package of claim 15, secured within a wearable electronic device.

19. A temperature sensor package comprising:
a routing layer including a top side and a bottom side;
a cavity formed in the bottom side of the routing layer;
a transducer mounted within the cavity;
an optical window over a surface of the transducer;
a chip mounted on the top side of the routing layer and in electrical connection with the transducer; and
an insulating layer encapsulating the routing layer and the chip.

20. The temperature sensor package of claim 19, further comprising a dielectric layer formed on the bottom side of the routing layer, wherein the optical window is arranged within an opening in the dielectric layer.

21. The temperature sensor package of claim 20, wherein the dielectric layer is secured to an enclosure made of metal shield, glass, or plastic.

* * * * *